US012751917B2

(12) United States Patent
Godfrin

(10) Patent No.: US 12,751,917 B2
(45) Date of Patent: Oct. 6, 2026

(54) HYDROGELS AS ORAL DELIVERY DOSAGE FORMS, METHODS OF MAKING AND USING SAME

(71) Applicant: Veramorph LLC, Mansfield, MA (US)

(72) Inventor: Paul Douglas Godfrin, Quincy, MA (US)

(73) Assignee: VeraMorph LLC, Mansfield, MA (US)

( * ) Notice: Subject to any disclaimer, the term of this patent is extended or adjusted under 35 U.S.C. 154(b) by 31 days.

(21) Appl. No.: 17/007,966

(22) Filed: Aug. 31, 2020

(65) Prior Publication Data

US 2021/0059933 A1 Mar. 4, 2021

Related U.S. Application Data

(60) Provisional application No. 62/893,529, filed on Aug. 29, 2019.

(51) Int. Cl.
*A61K 9/06* (2006.01)
*A61K 9/00* (2006.01)
*A61K 45/06* (2006.01)
*A61K 47/10* (2017.01)

(52) U.S. Cl.
CPC .............. *A61K 9/06* (2013.01); *A61K 9/0056* (2013.01); *A61K 47/10* (2013.01); *A61K 45/06* (2013.01)

(58) Field of Classification Search
CPC .......................... A61K 47/10; C08F 122/1006
See application file for complete search history.

(56) References Cited

U.S. PATENT DOCUMENTS

| | | | | |
|---|---|---|---|---|
| 5,124,421 | A | 6/1992 | Ulbrich et al. | |
| 7,056,901 | B2 | 6/2006 | Frechet et al. | |
| 9,644,039 | B2 | 5/2017 | Frechet et al. | |
| 10,214,479 | B2 | 2/2019 | Kosinski et al. | |
| 2003/0211158 | A1 | 11/2003 | Frechet et al. | |
| 2004/0076602 | A1* | 4/2004 | Harris | A61K 47/34 525/54.1 |
| 2004/0242770 | A1 | 12/2004 | Feldstein et al. | |
| 2006/0223776 | A1* | 10/2006 | Frechet | A61K 9/1635 424/487 |
| 2007/0277981 | A1 | 12/2007 | Robb et al. | |
| 2007/0281870 | A1 | 12/2007 | Robb et al. | |
| 2008/0305007 | A1* | 12/2008 | Cai | C09D 133/02 422/68.1 |
| 2009/0220615 | A1 | 9/2009 | Frechet et al. | |
| 2012/0039969 | A1 | 2/2012 | Bar-Shalom et al. | |
| 2013/0035635 | A1 | 2/2013 | Rau et al. | |
| 2013/0324704 | A1 | 12/2013 | Ye et al. | |
| 2018/0049999 | A1 | 2/2018 | Quay | |
| 2019/0388474 | A1 | 12/2019 | Aboody et al. | |
| 2020/0000734 | A1 | 1/2020 | Yu et al. | |
| 2021/0059933 | A1 | 3/2021 | Godfrin | |

FOREIGN PATENT DOCUMENTS

| | | | |
|---|---|---|---|
| CN | 101495149 | A | 7/2009 |
| CN | 102573913 | B | 7/2012 |
| JP | H10-72427 | A | 3/1998 |
| JP | 2013-523748 | A | 6/2013 |
| WO | WO 2006/105123 | A2 | 10/2006 |
| WO | WO 2011/012715 | A1 | 2/2011 |
| WO | WO 2011/123416 | A1 | 10/2011 |
| WO | 2021042043 | | 3/2021 |
| WO | WO 2022/187511 | A1 | 9/2022 |

OTHER PUBLICATIONS

Pohlit et al (Macromolecular Journals, 2017, 1600532, pp. 1-9) (Year: 2017).*
Pohlit et al (Biomacromolecules, 2015, vol. 16, pp. 3103-3111) (Year: 2015).*
Gao et al (ACS Nano, 2014, vol. 8, pp. 2900-2907) (Year: 2014).*
Vysotskaya et al (Russian Journal of Organic Chemistry, 2002, vol. 38, pp. 1133-1138) (Year: 2002).*
Kenworthy et al (Biophysical Journal, 1995, vol. 68, pp. 1903-1920) (Year: 1995).*
Schroder et al (Journal of Materials Chemistry B, 2015, vol. 3, pp. 7079-7089) (Year: 2015).*
McKenzie et al (Molecules, 2015, vol. 20, pp. 20397-20408) (Year: 2015).*
Shukla et al (Journal of Applied Polymer Science, 2009, vol. 111, pp. 1300-1310) (Year: 2009).*
Louguet et al (Acta Biomaterialia, 2014, vol. 10, pp. 1194-1205) (Year: 2014).*
Gillies et al (Journal of the American Chemical Society, 2004, vol. 126, pp. 11936-11943) (Year: 2004).*
Runarsdottir thesis (Use of modified PEG as a solubility enhancer for poorly soluble drugs: possible dosage forms and taste masking evaluation, Faculty of Pharmaceutical Sciences, School of Health Sciences, University of Iceland, May 2017) (Year: 2017).*
Kim et al (Polymer Degradation and Stability, 2015, vol. 121, pp. 303-310) (Year: 2015).*
Kharkar et al., "Designing Degradable Hydrogels for Orthogonal Control of Cell Microenvironments." Chemical Society Reviews 42(17):7335-7372 (2013).
Dingels et al. "Universal Concept for the Implementation of a Single Cleavable Unit at Tunable Position in Functional Poly (ethylene glycol)s," Biomacromolecules 14(2):448-459 (2013).
Kim et al. "Degradation Kinetics of Acid-Sensitive Hydrogels," Polymer Degradation and Stability 121 : 303-310 (2015).
Burek et al. "Hydrogels with Novel Hydrolytically Labile Trehalose-Based Crosslinks: Small Changes—Big Differences in Degradation Behavior," Polymer Chemistry 9(27): 3721-3726 (2018).

(Continued)

*Primary Examiner* — Mark V Stevens
(74) *Attorney, Agent, or Firm* — Leydig, Voit & Mayer, Ltd.

(57) ABSTRACT

Method of manufacturing, and use of cross-linked polymeric hydrogels as final dosage forms for the oral delivery of compounds with nutritional and/or therapeutic value, including but not limited to supplements, cell-based therapies, and active pharmaceutical ingredients.

30 Claims, 10 Drawing Sheets

(56) References Cited

OTHER PUBLICATIONS

Wang et al. "Preparation and Properties of Cyclic Acetal Based Biodegradable Gel by Thiol-Ene Photopolymerization," Materials Science and Engineering: C 33(3): 1261-1266 (2013).
Wang et al. "Preparation and Properties of Degradable Hydrogels Based on Diallyl Terminated Cyclic Acetal and PEG Monomer," Journal of Polymer Materials 31.1 (2014).
Kaihara et al., "Synthesis and properties of Poly [Poly (Ethylene Glycol)-Co-Cyclic Acetal] Based Hydrogels," Macromolecules 40(21): 7625-7632 (2007).
Huynh et al. "AcidDegradable Cross-Linked Micelles for the Delivery of Cisplatin: A Comparison with Nondegradable Cross-linker." Chemistry of Materials 24(16): 3197-3211 (2012).
Murthy et al., "A Novel Strategy for Encapsulation and Release of Proteins: Hydrogels and Microgels with Acid-Labile Acetal Cross-Linkers," Journal of the American Chemical Society 124(42): 12398-12399 (2002).
Wang et al. "Acid Degradable Poly (Vinylcaprolactam)-Based Nanogels with Ketal Linkages for Drug Delivery." Journal of Materials Chemistry B 3(28): 5824-5832 (2015).
Luan et al., "Hyaluronic-Acid-Based pH-Sensitive Nanogels for Tumor-Targeted Drug Delivery," ACS Biomaterials Science & Engineering 3(10): 2410-2419 (2017).
Parrott et al., "Tunable Bifunctional Silyl Ether Cross-Linkers for the Design of Acid-Sensitive Biomaterials," Journal of the American Chemical Society 132(50): 17928-17932 (2010).
Shieh et al., "Tailored Silyl Ether Monomers Enable Backbone-Degradable Polynorbornene-Based Linear, Bottlebrush and Star Copolymers through ROMP," Nature chemistry 11(12): 1124-1132 (2019).
Wei et al., "Smart pH-Sensitive Nanogels for Controlled Release in an Acidic Environment," Biomacromolecules 20(1):130-140 (2019).
Written Opinion and International Search Report for PCT/US2020/048772 (dated Mar. 4, 2021).
International Preliminary Report on Patentability for PCT/US2020/048772 (dated Mar. 1, 2021).
Sheehan et al., "USP Novel Excipients Survey: Stakeholders' Views on the Current State of Excipient Innovation," *Pharm Tech.*, 44:38-43 (2020).
Therasse et al., "New Guidelines to Evaluate the Response to Treatment in Solid Tumors. European Organization for Research and Treatment of Cancer, National Cancer Institute of the United States, National Cancer Institute of Canada," *J. Natl. Cancer Inst.*, 92:205-216 (2000).
Brazil Patent Office, Notification Preliminary Official Action Application No. 11 2022 003689 2 (Nov. 23, 2023).
China National Intellectual Property Administration, Office Action in Chinese Patent Application No. 202080061380.3 (Mar. 7, 2024).
Intellectual Property India, Office Action in Indian Patent Application No. 202227008742 (Dec. 13, 2023).
Japanese Patent Office, Notice of Reasons for Rejection Japanese Patent Application No. 2022-513542 (Jul. 8, 2024).
U.S. Patent and Trademark Office, International Preliminary Report on Patentability in International Patent Application No. PCT/US2022/018738, 8 pp. (Aug. 29, 2023).
U.S. Patent and Trademark Office, International Search Report in International Patent Application No. PCT/US2022/018738, 4 pp. (Jul. 1, 2022).
U.S. Patent and Trademark Office, U.S. Patent and Trademark Office, Written Opinion of the International Searching Authority in International Patent Application No. PCT/US2022/018738, 7 pp. (Jul. 1, 2022).

* cited by examiner

HYDROGELS AS ORAL DELIVERY DOSAGE FORMS, METHODS OF MAKING AND USING SAME

CROSS REFERENCE TO RELATED APPLICATIONS

This applications claims the benefit of priority of U.S. Provisional Patent Application Ser. No. 62/893,529, filed on Aug. 29, 2019, the entire contents of which are hereby incorporated by reference herein.

BACKGROUND OF THE INVENTION

This disclosure generally relates to the use of hydrolytically degradable cross-linked polymer gels (also referred to as disintegrating hydrogels) as oral dosages capable of encapsulating and orally delivering nutritional and/or therapeutic ingredients for nutritional, pharmaceutical, and/or veterinary purposes to a patient in need thereof.

Environmentally responsive hydrogels have previously been used for many purposes, including but not limited to drug delivery (U.S. Pat. No. 9,644,039B2), three-dimensional cell culture media (P. M. Kharkar, K. L. Kiick, & A. M. Kloxin, *Chem. Soc. Rev.*, 2013, 42, 7335), subterranean oil recovery (US20070281870A1, US20070277981A1), and curing epoxy resins (U.S. Ser. No. 10/214,479B2). Environmentally responsive polymers have also been designed for targeted drug delivery purposes (US20090220615A1) (C. Dingels, S. S. Müller, T. Steinbach, C. Tonhauser, H. Frey, *Biomacromolecules* 2013, 14, 448).

The chemistry of the cross-linkers enabling the responsiveness to the environmental conditions is varied, depending on the application and corresponding time scale of responsiveness. Examples of chemistries used within the life science field include silyl ethers, pentaerythritol, trimethyl orthoformate, and ketal functional groups covalently bound to hydroxyethyl(meth)acrylate as end groups (US20070281870A1; US20070277981A1; S. Kim, O. Linker, K. Garth, K. R. Carter, *Polym. Degrad. Stab.* 2015, 121, 303), ketal groups bound to amines as end groups cross-linked via di-epoxides (U.S. Ser. No. 10/214,479B2), ketal cross-linked poly-hydroxyl polymers such as poly (vinyl alcohol), poly(hydroxyethyl methacrylate), and polysaccharides using aldehydes, ketones, acetals, and/or vinyl ethers (U.S. Pat. No. 9,644,039B2), trehalose diacrylate with additional short linkages such as benzyl or hydroxyethyl groups (M. Burek, S. Waśkiewicz, A. Lalik, I. Wandzik, *Polym. Chem.* 2018, 9, 3721), cyclic acetals cross-linked via thiol-ene click chemistry (K. Wang, J. Lu, R. Yin, L. Chen, S. Du, Y. Jiang, Q. Yu, *Mater. Sci. Eng. C* 2013, 33, 1261; K. Wang, N. A. N. Zhang, J. Lu, R. Yin, J. U. N. Nie, Q. Yu, *J. Polym. Mater.* 2014, 31, 89) or free-radical polymerization methods (S. Kaihara, S. Matsumura, J. P. Fisher, *Macromolecules* 2007, 40, 7625), di-hydroxyethylmethacrylamide ketals formed with acetone (V. T. Huynh, S. Binauld, P. L. De Souza, M. H. Stenzel, *Chem. Mater.* 2012, 24, 3197) or a benzaldehyde derivative (U57056901 B2; N. Murthy, Y. X. Thng, S. Schuck, M. C. Xu, J. M. J. Fréchet, *J. Am. Chem. Soc.* 2002, 124, 12398), di-hydroxyethylacrylate acetone ketal (Y. Wang, J. Zheng, Y. Tian, W. Yang, *J. Mater. Chem. B* 2015, 3, 5824; S. Luan, Y. Zhu, X. Wu, Y. Wang, F. Liang, S. Song, *ACS Biomater. Sci. Eng.* 2017, 3, 2410), and silyl ethers bound to di-hydroxyethylacrylate (M. C. Parrott, J. C. Luft, J. D. Byrne, J. H. Fain, M. E. Napier, and J. M. DeSimone, *J. Am. Chem. Soc.* 2010, 132, 17928). Studies have also demonstrated the synthesis of polymers (not cross-linked) containing silyl ether functional groups capable of acid-catalyzed hydrolysis for degradation of polymers into smaller polymers (P. Shieh, H. V. T. Nguyen and J. A. Johnson, *Nature Chem.* 2019, 11, 1124).

BRIEF SUMMARY

This disclosure relates to the chemical composition, method of manufacturing, and use of cross-linked polymeric materials, known as hydrogels, as final dosage forms for the oral delivery, to a patient in need thereof, of compounds with nutritional, therapeutic, and/or veterinary value, including but not limited to supplements, cell-based therapies, and active pharmaceutical ingredients. The hydrogels comprise two primary constituents: backbone chains and hydrolytically degradable linkages that connect or cross-link them. This design uniquely facilitates both (1) the mechanically and chemically stable encapsulation of payload materials, such as food-grade or pharmaceutical-grade materials, within the pore space of the hydrogel between the backbone chains and (2) the rapid disintegration of the hydrogel structure through degradation (either through acid catalyzed hydrolysis or enzyme catalyzed cleavage) of the degradable linkages in acidic and/or neutral fluids, including but not limited to gastrointestinal fluids of the stomach and GI tract. The hydrogels are produced by polymerizing hydrolytically degradable cross-linkers containing the degradable linkage covalently bound to polymerizable groups that are converted to the backbone chains upon completion of the polymerization reaction. For the purposes of this disclosure, the definition of a hydrolytically degradable cross-linker (sometimes just referred to as a cross-linker) is a multi-functional chemical containing a hydrolytically degradable linkage (sometimes just referred to as a linkage), which is a chemical constituent containing 1 or more hydrolytically degradable functional groups, that is covalently bound to 2 or more polymerizable functional groups. Upon degradation of the linkage, the covalent bonds that attach it to the cross-linker's polymerizable functional groups are maintained. Therefore, the backbone chains are formed by the polymerizable functional groups of the cross-linkers as well as any additional polymerizable monomers (also referred to simply as monomers) that are present in solution during the polymerization reaction. The hydrophilic nature of the linkage component of the cross-linkers and their hydrolysis degradation products results in the release of water soluble polymers with a grafted/comb-like structure along with the payload materials of the hydrogel pores. Importantly, the cross-linker chemistry comprise biocompatible chemistries, such as, but not limited to, poly(ethylene glycol) (referred to also as PEG), that ensure low toxicity. If the backbone chains also contain hydrophobic alkyl chains, such as octadecyl acrylate, then the released comb-like polymers will have the characteristics of a surfactant, which will help improve the solubility of the payload, particularly pharmaceutical- and/or food-grade contents, of the hydrogel.

DETAILED DESCRIPTION

Figure 1:
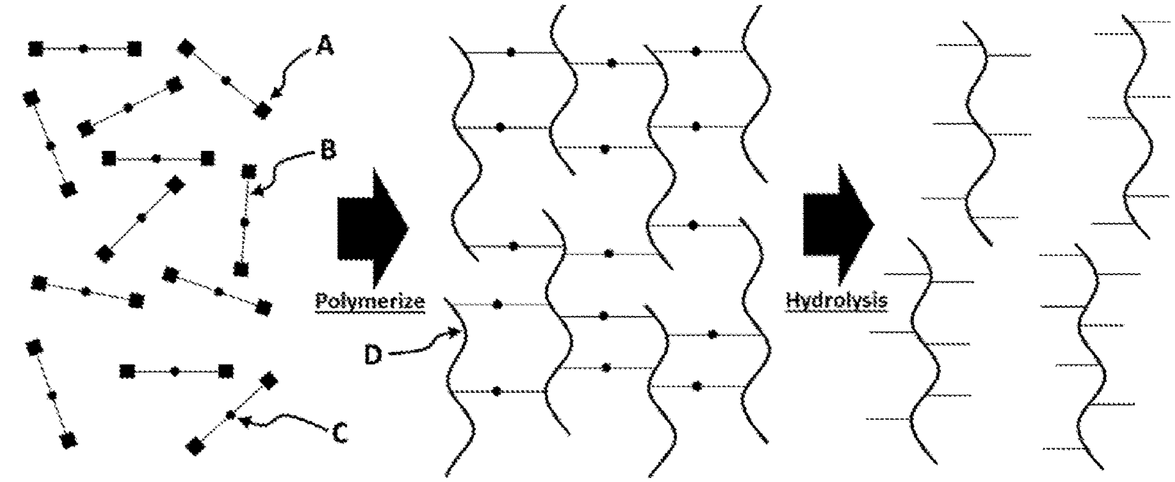
FIG. 1 is a schematic depiction of the polymerization and subsequent hydrolysis reactions of disintegrating hydrogels described herein.

This disclosure relates to the chemical composition, method of manufacturing, and use of cross-linked polymeric materials, known as hydrogels, as final dosage forms for the oral delivery, to a patient in need thereof, of compounds with nutritional, therapeutic, and/or veterinary value, including but not limited to supplements, cell-based therapies, and active pharmaceutical ingredients. The hydrogels comprise two primary constituents: backbone chains and hydrolytically degradable linkages that connect or cross-link them. This design uniquely facilitates both (1) the mechanically and chemically stable encapsulation of payload materials, such as food-grade or pharmaceutical-grade materials, within the pore space of the hydrogel between the backbone chains and (2) the rapid disintegration of the hydrogel structure through degradation (either through acid catalyzed hydrolysis or enzyme catalyzed cleavage) of the degradable linkages in acidic and/or neutral fluids, including but not limited to gastrointestinal fluids of the stomach and GI tract. The hydrogels are produced by polymerizing hydrolytically degradable cross-linkers containing the degradable linkage covalently bound to polymerizable groups that are converted to the backbone chains upon completion of the polymerization reaction. For the purposes of this disclosure, the definition of a hydrolytically degradable cross-linker (sometimes just referred to as a cross-linker) is a multi-functional chemical containing a hydrolytically degradable linkage (sometimes just referred to as a linkage), which is a chemical constituent containing 1 or more hydrolytically degradable functional groups, that is covalently bound to 2 or more polymerizable functional groups. Upon degradation of the linkage, the covalent bonds that attach it to the cross-linker's polymerizable functional groups are maintained. Therefore, the backbone chains are formed by the polymerizable functional groups of the cross-linkers as well as any additional polymerizable (also referred to simply as monomers) that are present in solution during the polymerization reaction. The hydrophilic nature of the linkage component of the cross-linkers and their hydrolysis degradation products results in the release of water soluble polymers with a grafted/comb-like structure along with the payload materials of the hydrogel pores. Importantly, the cross-linker chemistry comprise biocompatible chemistries, such as, but not limited to, poly(ethylene glycol) (referred to also as PEG), that ensure low toxicity. If the backbone chains also contain hydrophobic alkyl chains, such as octadecyl acrylate, then the released comb-like polymers will have the characteristics of a surfactant, which will help improve the solubility of the payload, particularly pharmaceutical- and/or food-grade contents, of the hydrogel.

Before the present compositions and methods are described in further detail, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention, which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to "a combustion chamber" is a reference to "one or more combustion chambers" and equivalents thereof known to those skilled in the art, and so forth.

As used herein, the term "about" means plus or minus 10% of the numerical value of the number with which it is being used. Therefore, "about 50" means "in the range of 45-55."

This disclosure relates to the chemical composition, method of manufacturing, and use of cross-linked polymeric materials, known as hydrogels, as final dosage forms for the oral delivery of a payload, which may include compounds with nutritional, therapeutic, and/or veterinary value, including but not limited to supplements, probiotics, cell-based therapies, and active pharmaceutical ingredients. The hydrogels comprise two primary constituents: backbone chains and hydrolytically degradable linkages that connect them. This design uniquely facilitates both (1) the mechanically and chemically stable encapsulation of a payload within the pore space of the hydrogel between the polymer chains and (2) the rapid disintegration of the hydrogel structure through degradation (either through acid catalyzed hydrolysis or enzyme catalyzed cleavage) of the linkages in acidic/neutral fluids, including but not limited to gastrointestinal fluids of the stomach and GI tract. Upon degradation of the linkages, the covalent bonds that attach it to the cross-linker's polymerizable functional groups are maintained. Therefore, the backbone chains are formed by the polymerizable functional groups of the cross-linkers as well as any additional monomers that are present in solution during the polymerization reaction. The hydrophilic nature of the cross-linkers ensures their hydration and subsequent degradation in aqueous solution, resulting in the release of water soluble polymers with a grafted/comb-like structure along with the payload of the hydrogel pores. In this manner, less water-soluble or insoluble payloads may be delivered to aqueous environments. If the backbone chains also contain hydrophobic alkyl chains, such as methyl methacrylate, ethyl methacrylate, butyl methacrylate, dodecyl methacrylate, or octadecyl methacrylate or their acrylate derivatives, then the released branched polymers will have amphiphilic characteristics (similar to a surfactant), which will help improve the solubility of the payload of the hydrogel. Some embodiments include:

A hydrogel matrix containing a hydrolytically degradable cross-linker capable of disintegration into water-soluble degradation products in acidic to neutral buffers. For immediate release, degradation should occur within 2 hours while release at specific GI tract locations can be tailored by tuning the degradation rate and sensitivity to pH.

A sufficiently hydrophobic hydrogel matrix that is hydrolytically degradable, used to encapsulate a payload, such as an organic liquid solution in the matrix and for subsequent release for nutritional and/or therapeutic effect.

An amphiphilic polymer chemistry released upon hydrogel degradation resulting in characteristics similar to a surfactant molecule that can improve the solubility of the payload released from the hydrogel concomitantly with the hydrogel degradation products. Examples of amphiphilic polymer structures include, but are not limited to, a hydrophobic polymer backbone (e.g. polymethacrylate) grafted with hydrophilic chains (e.g., polyethylene glycol) or a hydrophilic polymer backbone (e.g., polyvinylpyrrolidone) grafted with hydrophobic chains (e.g., butyl acrylate).

A suitable hydrogel matrix contains single- or multi-component backbone polymer chains connected by hydrolytically degradable linkages covalently linked to said polymer chains. Single-component polymer chains are released upon hydrogel degradation when the hydrogels only contain the cross-linkers, whereby the backbone chains consist of the polymerizable functional groups of the cross-linker. Multi-component polymer chains are released from the degradation of hydrogels that contain cross-linkers and additional monomers.

Examples of chemistries that can be used as monomers (i.e., additional polymer components) include methacrylic acid, methyl methacrylate, ethyl methacrylate, butyl methacrylate, dimethylaminoethyl methacrylate, methacrylamide, hydroxyethyl methacrylate, 2-(methacryloyloxy)ethyl trimethylammonium chloride, poly(ethylene glycol) methacrylate, cetyl methacrylate, lauryl methacrylate (or the acrylate derivative of any methacrylate component), 2-Acrylamido-2-methylpropane sulfonic acid, vinyl phosphonic acid, N-vinyl caprolactam, N-vinyl pyrrolidone, vinyl acetate, and vinyl alcohol by themselves or as co-polymers with any combination thereof.

The cross-linker contains at least one hydrolytically degradable functional group within the linkage that degrades under acidic and/or neutral conditions ranging in pH from 0 to 8, from 1 to 7, from 1 to 5, or from 1 to 4.

Exemplary hydrolytically degradable functional groups contained within the cross-linker(s) include but are not limited to acetal, anhydride, boronate ester, enamine, hydrazone, imide, imine, ketal, oxime, alkyl silyl ether, and silyl ether functional groups.

In some embodiments, the hydrolytically degradable linkage contains at least one of either a ketal, acetal, alkyl silyl ether, or silyl ether functional group as the degradable functional group(s). In the case of multiple silyl ether functional groups, they may be separated from each other, such as by poly(ethylene glycol), or be structured adjacent to each other in a multi-unit segment, such as poly(dimethyl siloxane).

In some instances, the hydrolytically degradable linkage is poly(ethylene glycol)-based.

In some embodiments, the hydrolytically degradable cross-linker comprises one or two silyl ethers, alkyl silyl ethers, or polysiloxanes as the hydrolysable functional group (s). Either the use of a single silyl ether or a polysiloxane can be covalently bound to two poly(ethylene glycol) methacrylate moieties (see formula I below).

I

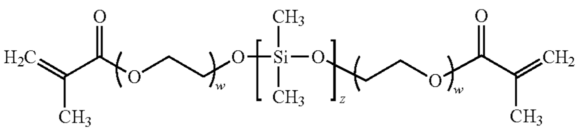

wherein:

z is the number of polydimethylsiloxane repeat units, where a single silyl ether is represented by z=1 and a polysiloxane by z≥2, and w represents the number of polyethylene glycol units between the hydrolysable functional group and the polymerizable functional group, where w≥2.

In some embodiments, z is between 3 and 7, which can enable the formation of cyclomethicones after hydrolysis of the two alkyl silyl ether groups on either side of the linear polydimethylsiloxane entity. Therefore, the z value can range from between 2 and 1000, 2 and 100, 2 and 20, 3 and 20, 3 and 10, 3 and 7, 4 and 7, 4 and 6, or 4 and 5.

An embodiment containing two silyl ether groups or two polysiloxane segments separated from each other by a linker can consist of a central polyethylene glycol unit bound on both sides to diemthylsiloxane functional groups which are each also bound to polyethylene glycol methacrylate functionalities (see formula II below).

II

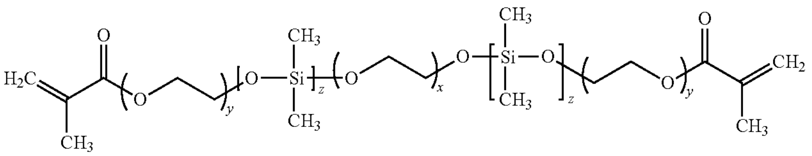

The number of repeat units of the central polyethylene glycol linker separating the two hydrolysable groups (with the embodiment shown in formula II having either silyl ether groups for z=1 or polysiloxane groups for z≥2 or a mix of the two) is represented by the parameter x and can vary from 1 to 1,000, 1 to 100, 1 to 50, 3 to 50, 3 to 25, or 3 to 10. The number of repeat units of the polyethylene glycol chain separating a polymerizable functional group (represented by a methacrylate group in formula II below) and a hydrolysable group is represented the parameter y, where y can vary from 1 to 1,000, 1 to 100, 1 to 50, 2 to 50, 2 to 25, 2 to 10, 3 to 25, or 3 to 10.

Certain hydrolysable functional groups are anisotropic in that they only have one covalent bond that can be hydrolyzed. One embodiment of this type of cross-linker, where the single anisotropic hydrolysable group is an alkyl silyl ether, can consist of poly(ethylene glycol) methacrylate bound to a methacryloylpropyl dimethylsilane group (see formula III below).

III

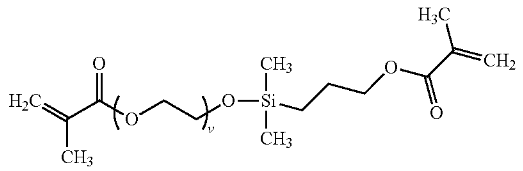

In formula III, the parameter v represents the number of polyethylene glycol repeat units separating the polymerizable group (a methacrylate functional group in formula III) and the anisotropic hydrolysable group, where v can vary from 1 to 1,000, 1 to 100, 1 to 50, 1 to 25, 1 to 10, 2 to 50, 2 to 25, 2 to 10, 3 to 50, 3 to 25, or 3 to 10.

One embodiment containing two anisotropic hydrolysable groups, where both are alkyl silyl ether groups, can consist of two methacryloylpropyl dimethylsilane groups bound to a poly(ethylene glycol) moiety (see formula IV below) of any molecular weight, but preferably large enough to create a pore size sufficient to achieve high drug loading. The parameter x is the same as defined previously in formula II designating the number of repeat units of polyethylene glycol separating two hydrolysable groups within the cross-linker.

IV

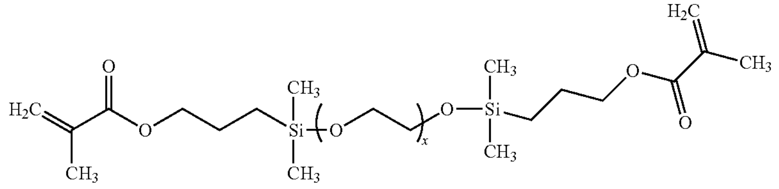

In some embodiments, the hydrolytically degradable cross-linker contains acetal and/or ketal hydrolysable functional groups instead of silane based hydrolysable functional groups as discussed previously. One embodiment comprises a central poly(ethylene glycol) segment of molecular weight no less than about 150 g/mol (equivalent to the parameter x equal to or greater than 3) with both terminal hydroxyl groups attached to an acetaldehyde group, which is an acetal functional group, that is simultaneously bound to a PEG methacrylate group with a molecular weight no less than about 174 g/mol (equivalent to the parameter y equal to or greater than 2) (see formula V, below).

V

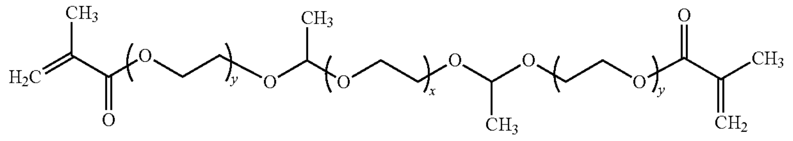

In some embodiments, the structure of the acid-catalyzed hydrolysable cross-linker contains two hydrolysable ketal functional groups and two polymerizable methacrylate functional groups.

In some embodiments, the cross-linker is triethylene glycol di[ethyl-1-methacryloyloxy poly(ethylene glycol) acetal], which is equivalent to formula V below with the parameter x=3 and parameter y=9. This cross-linker forms effective disintegrating hydrogels when formulated in a pre-cursor solution (prior to polymerization of the polymerizable functional groups) at concentrations equal to or above about 10% by volume to ensure the formation of a mechanically stable polymer network and at concentrations equal to or below about 35% by volume to ensure hydrolytic disintegration of the polymer network in order to achieve about complete release of a payload encapsulated within the pores of said network. Compositions containing concentrations above about 35% are the subject of future experimentation.

Other suitable cross-linkers include, but are not limited to: acetone di[methacryloyloxy poly(ethylene glycol)] ketal (see formula VI below) and acetaldehyde acryloyloxyethanol methacryloyloxypoly(ethylene glycol) acetal (see formula VII below).

VI

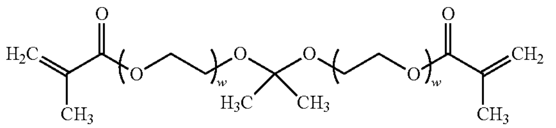

-continued

VII

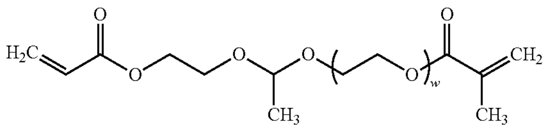

The parameter w is identical to that described previously for hydrolysable cross-linkers that contain silane based hydrolysable functional groups. The embodiment shown in formula VII is an example of an anisotropic hydrolysable cross-linker where the value of parameter w on one side of the hydrolysable functional group is 1 and on the other it can be any number as described in the ranges presented previously. Hydrogels made from acetaldehyde acryloyloxyethanol methacryloyloxypoly(ethylene glycol) acetal do not fully degrade when the volume fraction of the cross-linker is above about 20% in the pre-cursor solution during synthesis. The exact mechanism (e.g., steric hindrance, a fast reverse reaction, etc.) preventing hydrolysis is uncertain.

Other cross-linkers include: acetone di(hydroxyethyl acrylate) ketal (see formula VIII below) and acetone di(hydroxyethyl methacrylate) ketal (see formula IX below). Without wishing to be bound by theory, the close proximity of the hydrolysable ketal functional group to the polymerizable functional groups of these cross-linkers hinders, but does not prevent, the acid catalyzed hydrolysis reaction, which causes slower drug release. Also, the small molecular weight of the cross-linker reduces swelling in the presence of organic solvent and therefore results in lower payloads to be encapsulated in the pores of the hydrogel.

VIII

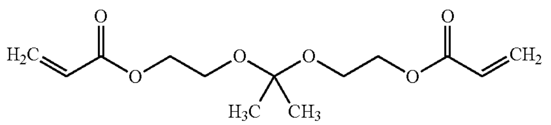

-continued

IX

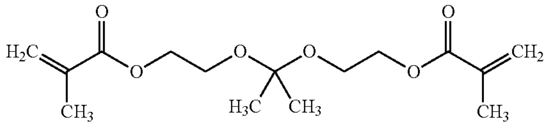

Hydrogels can contain between 0.1% and 100% by mole of cross-linker with the remainder composed of monomers between 0% and 99.9%, or between 1% and 50%, or between 5% and 25%, or between 10% and 20%.

In one embodiment, a hydrogel composition contains 20% by mole of the triethylene glycol di[ethyl-1-methacryloyloxy poly(ethylene glycol) acetal] cross-linker, 40% by mole of methyl methacrylate, and 40% by mole of dimethylaminoethyl methacrylate.

In hydrogel composition contains 100% by mole of triethylene glycol di[ethyl-1-methacryloyloxy poly(ethylene glycol) acetal] cured into a hydrogel at 25% by volume in solution.

Hydrolysable Hydrogels Containing Active Ingredients as an Oral Dosage Form

In some instances, the hydrolysable hydrogel contains a payload comprising a nutritional supplement, active pharmaceutical ingredient, cell-based supplement or cell-based therapy as well as additional inactive ingredients, including but not limited to solvent, oils/lipids, surfactants, and polymers, such that it can serve as an oral dosage form for these materials.

Hydrophobically Modified Hydrolysable Hydrogels that Degrade into Surfactant-Like Amphiphilic Molecules In some instances of disintegrating hydrogels with 100% cross-linker, the polymer chains released upon the hydrolysis of the hydrolysable functional groups contain hydrophobic backbones, such as methacrylate functional groups, with hydrophilic chains, such as polyethylene glycol, covalently bound to them in a comb-like structure that possesses the qualities of an amphiphilic molecule.

A preferred embodiment of this chemical composition is formed by the hydrolysis of disintegrating hydrogels composed initially of triethylene glycol di[ethyl-1-methacryloyloxy poly(ethylene glycol) acetal] (formula V above), which transforms into individual chains of poly(polyethylene glycol methacrylate) that are difficult to synthesize via other methods of polymerization.

In some instances, the polymer chains contain hydrophobic monomers (or ligands covalently bound to them) of between 1% to 90% by mole, or between 10% to 75% by mole, or between 20% to 50% by mole.

Upon degradation of such compositions, the resulting grafted polymer chains are soluble in aqueous solutions and have the properties of an amphiphilic molecule.

The chemical composition of the hydrolysis product and a schematic of the process by which this hydrolysis product is formed are provided in FIG. 1. As shown, the hydrolysable cross-linkers polymerize into a cross-linked polymer network that comprises disintegrating hydrogels which subsequently hydrolyze into individual comb-like polymers. The components of the hydrolysable cross-linkers are labeled as: the polymerizable functional group is labeled A, the linkage between the polymerizable functional groups is labeled B, and the hydrolysable functional group within the linkage is labeled C. After polymerization, the polymerizable functional groups are transformed into the backbone polymer chains, labeled D, of the cross-linked network comprising the disintegrating hydrogel. Upon hydrolysis, the hydrolysable functional group is removed, resulting in individual polymer chains.

In some instances, the hydrophobic ligand is a medium to large alkyl chain with a polymerizable end group. In some instances, the hydrophobic ligands are either ethyl methacrylate, butyl methacrylate, octyl (capryl) methacrylate, dodecyl (lauryl) methacrylate, or octadecyl (stearyl) methacrylate or their acrylate derivatives.

In some instances, the hydrophobic ligand is a non-ionic surfactant, such as but not limited to alkyl PEG ethers, PEG-PPG-PEG triblock co-polymers, and fatty acid PEG esters, modified to include a polymerizable functional group, which is referred to as a polymerizable surfactant. In some embodiments, these monomers contain a hydrolysable functional group to which both a non-ionic surfactant and a polymerizable functional group are covalently bound, which is referred to as hydrolysable surfactant monomers. In some embodiments, the surfactant is an alkyl poly(ethylene glycol) ether, such as but not limited to PEG-20 stearyl ether. Hydrogels containing polymerizable surfactants retain the hydrophobic characteristics of the surfactant within the polymers released after hydrolysis while hydrogels containing hydrolysable surfactant monomers release the surfactant and comb-like polymers separately upon decomposition of the hydrolysable functional groups.

Hydrophobically Modified Hydrolysable Hydrogels Loaded with a Lipid Based Formulation Containing an Active Pharmaceutical Ingredient In some embodiments, the void space of the hydrogel contains a payload comprising a self-emulsifying or spontaneous micelle forming lipid solution that may include an organic solvent, a hydrophobic solvent (oil), a surfactant, and a co-surfactant either alone or in any possible combination. In some embodiments, the lipid solution payload also contains an active pharmaceutical ingredient.

Figure 2:
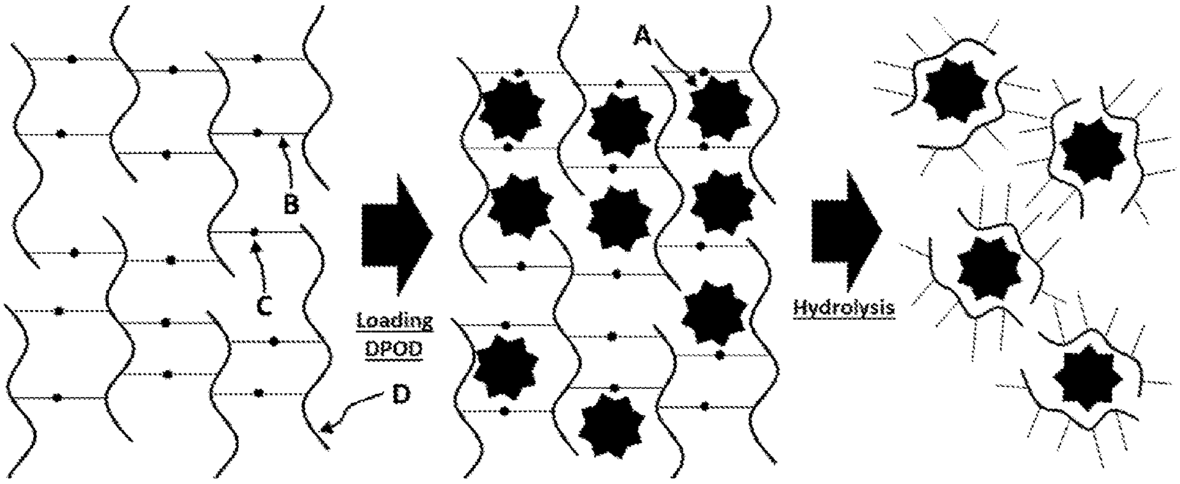
FIG. 2 is a schematic depiction of the drug loading and drug release of a payload within disintegrating hydrogels.

Method of Making Hydrolysable Hydrogels and Loading them with Active Ingredients FIG. 2 is a schematic depiction of the drug loading and drug release of a payload within disintegrating hydrogels. The payload is labeled A, the linkage connecting the backbone polymer chains is labeled B, the hydrolysable functional group within the linkage is labeled C, and the backbone polymer chain is labeled D. After loading, the payload sits within the pores of the cross-linked polymer network. After hydrolysis, the amphiphilic comb-like polymer chains associate with the payload to improve solubility.

In some embodiments, the hydrogels contemplated herein are produced by combining a polar (protic or aprotic) solvent with a hydrolytically degradable cross-linker and an initiator (e.g., photo-initiator, thermo-initiator, etc.) in a homogeneous solution, then added into an inert mold of a given shape and exposed to an initiation source (e.g., UV lamp, heating element, etc.) for a necessary period of time to induce sufficient polymerization of the cross-linker into a mechanically stable cross-linked hydrogel.

In some embodiments, the starting solution contains between 15% and 35% by volume of the cross-linker triethylene glycol di[ethyl-1-methacryloyloxy poly(ethylene glycol) acetal] and about 5% by volume of the photoinitiator 2-hydroxy-2-methylpropiophenone dissolved in dimethylformamide, which is then dispersed into a silicone mold and exposed to a 365 nm wavelength lamp for 20 minutes.

This chemical composition of this hydrogel is provided as Formula X, below:

X

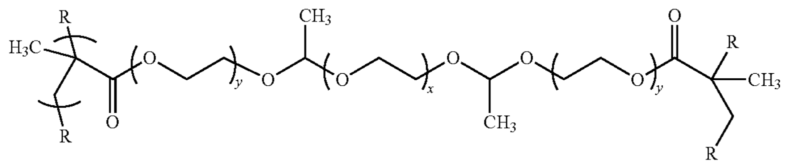

Disintegrating hydrogels containing the structure shown in Formula X, in some embodiments, a composition that is 100% by mole of the cross-linker triethylene glycol di[ethyl-1-methacryloyloxy poly(ethylene glycol) acetal], will transform into comb-like polymers with the structure shown in Formula XI below, specifically poly(polyethylene glycol methacrylate) polymers, upon hydrolysis of the hydrolysable functional groups. The molecular weight of the resulting comb-like polymers, of this or any other composition, released upon hydrogel disintegration can vary from 1,000 g/mol up to 1,000,000 g/mol. Byproducts of the disintegration of hydrogels containing the structure in Formula X include triethylene glycol and acetaldehyde.

XI

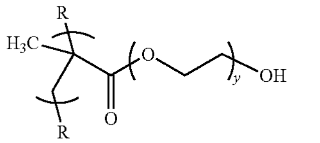

In some embodiments, the hydrogels contemplated herein are produced by combining a polar (protic or aprotic) solvent with mono-functional monomers, di-functional hydrolytically degradable cross-linkers, and an initiator (e.g., photo-initiator, thermo-initiator, etc.) in a homogeneous solution, then added into an inert mold of a given shape and exposed to an initiation source (e.g., UV lamp, heating element, etc.) for a necessary period of time to induce sufficient polymerization of the functional components into a mechanically stable cross-linked hydrogel.

In some embodiments, the starting solution contains about 20% by volume of the cross-linker triethylene glycol di[ethyl-1-methacryloyloxy poly(ethylene glycol) acetal], about 10% by volume of an equimolar solution of dimethylaminoethyl methacrylate and methyl methacrylate, and about 5% of the photoinitiator 2-hydroxy-2-methylpropiophenone dissolved in dimethylformamide, which is then dispersed into a silicone mold and exposed to a 365 nm wavelength lamp for 20 minutes.

The chemical structure of one embodiment of a chemically cross-linked hydrogel containing the preferred acid-labile cross-linker triethylene glycol di[ethyl-1-methacryloyloxy poly(ethylene glycol) acetal] with a hydrophobic monomer (alkyl methacrylate) and two other monomeric constituents (methyl methacrylate and dimethylaminoethyl methacrylate) that promote hydration, swelling, and solubilization in an aqueous solution. This chemical composition of this hydrogel is provided as Formula XII, below. The parameters x and y are the same as described previously and the parameter u represents the number of repeat methyl units within an alkoxymethacrylate monomer between the methacrylate group and a terminal methyl group that can vary from between 0 and 21, or 1 and 17, or 3 and 17. The parameter R refers to any other monomeric units and/or functional groups used for initiation and termination of the polymerization process, such as the photoinitiator and solvent, respectively.

XII

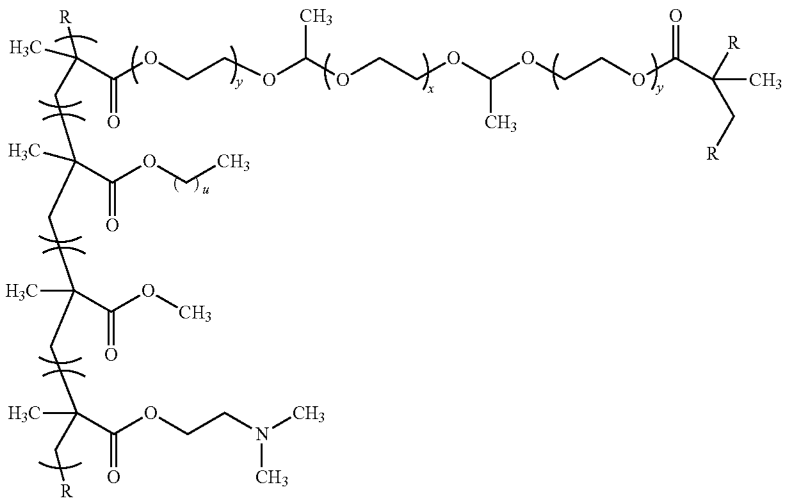

This composition yields a hydrogel that, after washing to remove unreacted monomers and photoinitiator, will completely hydrolyze and dissolve in no more than 30 minutes when added to an aqueous buffer at pH 1, provided that the size of the smallest dimension of the hydrogel is on the order of 10 mm or less.

The cross-linked hydrogel with the composition of formula XII will transform upon exposure to an acidic aqueous solution, due to the hydrolysis of the acetal functional groups within the linkage, into individual polymer chains with the composition shown in formula XIII.

XIII

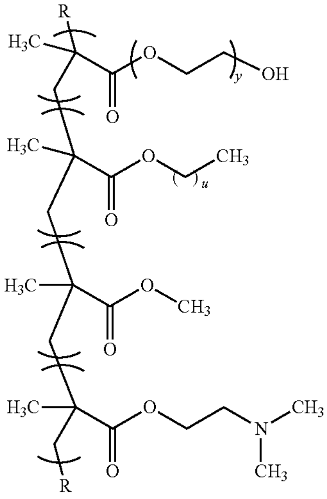

In some embodiments, the starting solution contains between 15% and 30% by volume of the cross-linker triethylene glycol di[ethyl-1-methacryloyloxy poly(ethylene glycol) acetal], between 1% and 20% by volume of a hydrolysable surfactant monomer, and about 5% by volume of the photoinitiator 2-hydroxy-2-methylpropiophenone dissolved in dimethylformamide, which is then dispersed into a silicone mold and exposed to a 365 nm wavelength lamp for 20 minutes. The resulting chemical structure of this disintegrating hydrogel is shown in Formula XIV, below. The parameters x, y, u, and R are the same as described previously and the parameter q represents the number of repeat polyethylene glycol units contained within the surfactant molecule, which can vary from 2 to 100 or from 4 to 20. The cross-linked hydrogel with the composition of formula XIV will transform upon exposure to an acidic aqueous solution, due to the hydrolysis of the acetal functional groups within the linkage, into individual polymer chains with the composition shown in Formula XI, but potentially with monomers having different values of the parameter y as a result of different compositions of the hydrolysable surfactant and hydrolysable cross-linker using during hydrogel synthesis. Byproducts of the disintegration of hydrogels containing the structure in Formula XIV include triethylene glycol, acetaldehyde, and the non-ionic surfactant used to synthesize the hydrolysable surfactant monomer.

XIV

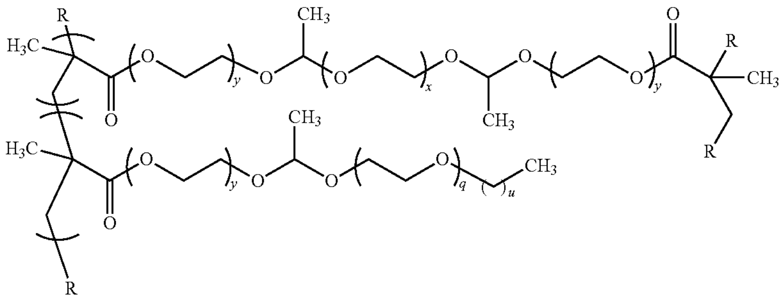

A method of loading a dietary ingredient or an active pharmaceutical ingredient into a disintegrating hydrogel synthesized by the process described above, where the given active ingredient is dissolved in a polar (protic or aprotic) solvent and this solution is added to a mold containing the hydrogel and the solvent is evaporated to concentrate the active ingredient into the pore space of the hydrogel and eventually remove all or essentially all of the solvent.

This process results in the transformation of a payload, such as a dietary ingredient or an active pharmaceutical ingredient with a melting temperature above about 20° C. (i.e., a solid at room temperature), into nanocrystals with an average size of between 10 nm and 1000 nm, 10 nm and 500 nm, 10 nm and 300 nm, 10 nm and 100 nm, 20 nm and 500 nm, 20 nm and 300 nm, 20 nm and 100 nm, less than 300 nm, less than 200 nm, less than 100 nm, or less than 50 nm.

The result of following this process is the formation of a hydrolysable hydrogel loaded with a poorly soluble drug that can subsequently release that drug in an acidic aqueous solution at pH 1 in under 240 minutes, or under 120 minutes, or under 90 minutes, or under 60 minutes, or under 40 minutes, or under 30 minutes to a solubility that is larger than the saturation concentration of the drug by itself.

The drug loading process described previously can also be accomplished with a polar (aprotic or protic) solvent that contains a lipid based formulation mixture (including but not limited to a glyceride, surfactant, and co-surfactant and/or co-solvent) in addition to an active pharmaceutical ingredient such that, upon solvent removal, the lipid based formulation and the active pharmaceutical ingredient are encapsulated in the pore space of the disintegrating hydrogel. The resulting disintegrating hydrogel drug product will release solubilizing polymers, lipid formulation ingredients, and the active pharmaceutical ingredient in the form of an emulsion to improve solubility of the active pharmaceutical ingredient (see FIG. 1).

Loading a disintegrating hydrogel with cell-based therapies is accomplished by adding the desired cells to the pre-cursor solution of a polar solvent, a cross-linker, and an initiator prior to the polymerization reaction. Subsequent exposure to an initiation source will cause the cross-linker to polymerize into a hydrogel with the cells encapsulated in the pore space of said hydrogel.

By controlling the concentration of the active pharmaceutical ingredient, nutritional supplement, veterinary ingredient, and/or cell-based therapy in solution during the loading process, the mass fraction of that payload within the disintegrating hydrogel (i.e. the mass of the payload divided by the combined mass of the payload and the hydrogel) can be controlled to be between 1% and 99%, 5% and 90%, 10% and 90%, 15% and 80%, 20% and 70%, 20% and 60%, 20% and 50%, 30% and 70%, 30% and 60%, or 30% and 50%.

The chemical versatility of hydrolysable hydrogels makes them the most widely compatible oral dosage form for poorly soluble active pharmaceutical ingredients. The chemical composition of the hydrogel, including the cross-linker and any and all monomers, can be modified to maximize the chemical compatibility with any chemical payload, especially active pharmaceutical ingredients. The solvent used to dissolve the payload, such as an active pharmaceutical ingredient and its concentration in that solution can also be adjusted to maximize the swelling of the hydrogel and consequently the amount (either by mass or volume) of payload capable of being infused into the pores of the hydrogel. This has been conducted with several active pharmaceutical ingredients spanning a wide range of chemical properties critical to the solubility and absorption during oral drug delivery, including the lipophilic partition coefficient (Log P) ranging from 0.8 to 10.5, the melting temperature (Tm) ranging from −54° C. to 301° C., molecular weight (Mw) ranging from 206 g/mol to 1203 g/mol, and aqueous solubility (C_s) ranging from 0.01 μg/mL to 120 μg/mL. Disintegrating hydrogel oral dosages have also been shown to be compatible with a wide range of chemical classes, including but not limited to kinase inhibitors, statins, hormones, antioxidants, macrolides, NSAIDs, anti-infectives, and hyperlipidemics. The drugs tested and their corresponding parameters are summarized in Table 1. In addition to the drugs listed in Table 1, examples of active pharmaceutical ingredients that are compatible with hydrolytically degradable hydrogels within the NSAID class include acetylsalicylic acid, naproxen, fenoprofen, ketoprofen, flurbiprofen, indomethacin, diclofenac, aceclofenac, mefenamic acid, tolfenamic acid, and piroxicam; within the anti-infective class include vancomycin, clindamycin, erythromycin, linezolid, tigecycline, doxycycline, ritonavir, lopinavir, tenofovir, rilpivirine, efavirenz, itraconazole, ketoconazole, griseofulvin, and miconazole; within the antioxidant class include beta-carotene, ubiquinones, lycopene, phytomenadione, menadione, calciferol, cholecalciferol, and curcumin; within the cannabinoid class include tetrahydrocannabinol, cannabinol, cannabigerol, cannabichromene, cannabielsoin, and cannabicyclol; within the antihyperlipidemic class include icosapent ethyl, docosahexaenoic acid, bempedoic acid, clofibride, simfibrate, and gemfibrozil; within the statin class include rosuvastatin, fluvastatin, lovastatin, simvastatin, and pravastatin; within the kinase inhibitor class include vemurafenib, regorafenib, osimertinib, imatinib, sorafenib, ibrutinib, erlotinib, dasatinib, olaparib, lenvatinib, and gefitinib; within the macrolide class include erythromycin, daptomycin, clarithromycin, carbomycin A, spiramycin, tacrolimus, sirolimus, nystatin, cruentaren, natamycin, and mycolactone; within the retinoid class include retinol, etretinate, acitretin, bexarotene, and adapalene; and within the steroidal hormone class include estradiol, ethinyl estradiol, etonogestrel, mifepristone, testosterone, dexamethasone, prednisone, ganaxalone, brexanolone, pregnenolone, abiraterone acetate, levonorgestrel, budesonide, and fluticasone furoate.

TABLE 1

| Drug | % wt drug | X_sat | Class | log P | Tm (° C.) | Mw (g/mol) | C_s (μg/mL) |
|---|---|---|---|---|---|---|---|
| anthraquinone | 7.8 | 3.88 | anthracycline | 3.4 | 286 | 208.2 | 1.34 |
| albendazole | 18.8 | 2.01 | anti-infective | 2.7 | 208 | 265.3 | 22.8 |
| clofazimine | 18.7 | 11.2 | anti-infective | 7.66 | 210 | 473.4 | 0.23 |
| lumefantrine | 20.7 | 12.8 | anti-infective | 8.34 | 128 | 528.9 | 0.04 |
| tocopherol (vitamin E) | 63.2 | 73.9 | antioxidant | 10.5 | 3 | 430.7 | 0.01 |
| Coenzyme Q10 | 15.5 | 69.1 | antioxidant | 9.9 | 48 | 863.3 | 0.2 |
| cannabidiol (CBD) | 26.2 | 22.3 | cannabinoid | 6.1 | 63 | 314.5 | 12.6 |
| eicosapentaenoic acid | 34 | 505 | antihyperlipidemic | 6.1 | −54 | 302.5 | 0.29 |
| fenofibrate | 31.7 | 351 | antihyperlipidemic | 5.3 | 81 | 360.8 | 0.71 |
| nilotinib | 26.3 | 1.63 | kinase inhibitor | 4.51 | 238 | 529.5 | 2.01 |
| pazopanib | 8.9 | 1.27 | kinase inhibitor | 3.59 | 301 | 437.5 | 43.3 |
| amphotericin b | 31.5 | 13.8 | macrolide | 0.8 | 170 | 924.1 | 82 |
| cyclosporin | 34.4 | 6.4 | macrolide | 1.4 | 148 | 1202.6 | 40 |
| diflunisal | 21.7 | 9.96 | NSAID | 4.44 | 210 | 250.2 | 14.5 |
| ibuprofen | 42.4 | 2.58 | NSAID | 3.97 | 77 | 206.3 | 21 |
| retinoic acid (tretinoin) | 26.1 | 4.05 | retinoid | 6.3 | 181 | 300.4 | 4.8 |
| atorvastatin | 19.7 | 1.38 | statin | 6.36 | 176 | 558.6 | 0.63 |
| methylprednisolone | 15.6 | 1.81 | steroid hormone | 1.53 | 233 | 374.5 | 120 |
| progesterone | 22.7 | 11.2 | steroid hormone | 3.87 | 130 | 314.5 | 5.5 |
| | | | Minimum | 0.8 | −54 | 206.3 | 0.01 |
| | | | Maximum | 10.5 | 301 | 1202.6 | 120 |

FIGS. 3-19 are dissolution profiles of the above listed payloads.

Example 1—Synthesis of the Di-Acetal Cross-Linker Triethylene Glycol Di[Ethyl-1-Methacryloyloxy Poly(Ethylene Glycol) Acetal]

Synthesis of cross-linkers described above where a poly (ethylene glycol) divinyl ether is added with 2 molar equivalents of poly(ethylene glycol) methacrylate to dichloromethane containing toluenesulfonic acid as a catalyst and allowed to react for 1 hour at 25° C. The reaction is quenched with the addition of 5 molar equivalents of triethylamine to the toluenesulfonic acid. The reaction solution is washed with an equal volume of 1M sodium hydroxide solution to extract the triethylammonium toluenesulfonate salt and excess triethylamine. The remaining reaction solution is dried to remove residual water then the product is purified by removing dichloromethane via evaporation.

Example 2—Synthesis of a Disintegrating Hydrogel Using a Di-Acetal Based Cross-Linker A pre-cursor solution was made by dissolving the cross-linker triethylene glycol di[ethyl-1-methacryloyloxy poly (ethylene glycol) acetal] and the photoinitiator 2-hydroxy-2-methylpropiophenone in dimethylformamide, a volume percentage of 25% and 5%, respectively. Once mixed to a homogeneous solution, it is then dispensed into a silicone mold and exposed to a 365 nm wavelength lamp for 20 minutes. The semi-solid disintegrating hydrogels are then mechanically removed from the mold and soaked in a volume of ethanol 5 times the volume of the gels three consecutive times to ensure the level of residual monomers, photoinitiator, and dimethylformamide is well below 1% the original content of each component.

Example 3—Lumefantrine in Disintegrating Hydrogels

Figure 6:
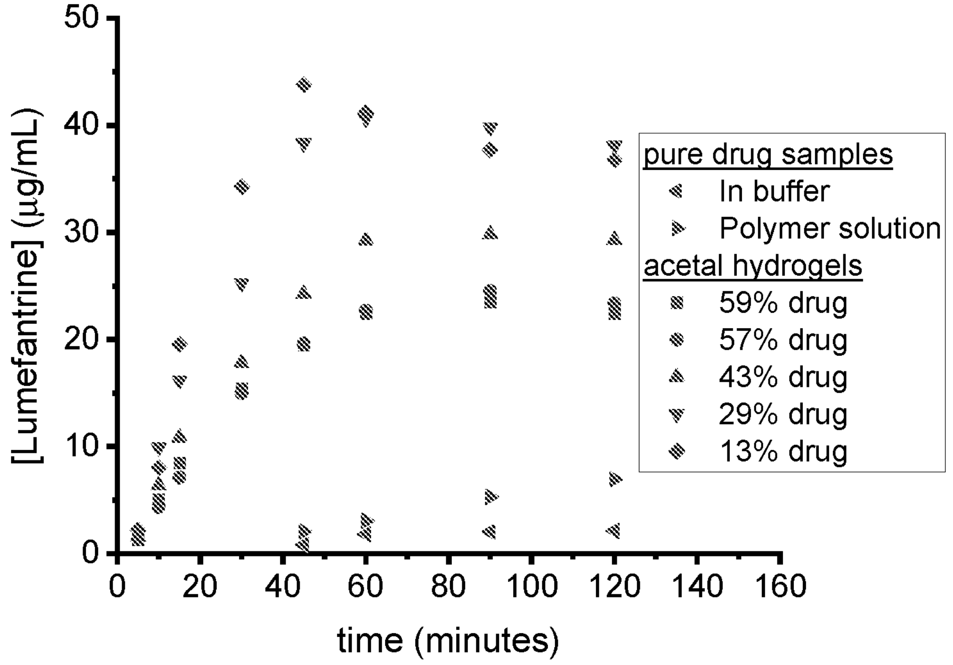
FIG. 6 is a dissolution profile of the concentration of lumefantrine released into simulated gastric fluid from disintegrating hydrogel tablets composed of 25% by volume acetal cross-linker with several different drug loading levels as compared to pure crystalline lumefantrine (labelled "in buffer"). For comparison, the figure includes the dissolution profile of pure crystalline lumefantrine released into a solution of pre-disintegrated hydrogel tablets in simulated gastric fluid (labelled "polymer solution").
Figure 7:
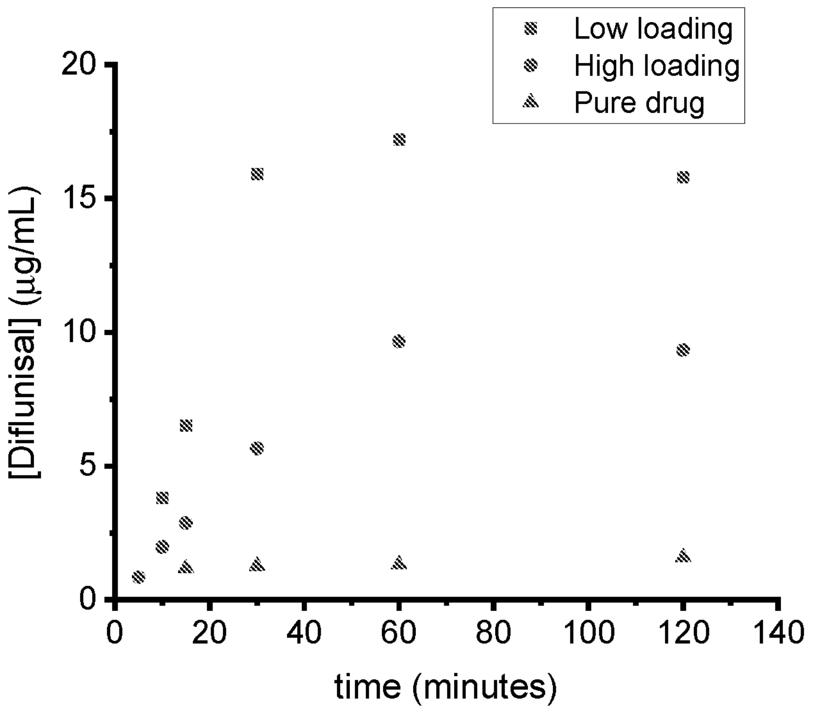
FIG. 7 is a dissolution profile of the concentration of diflunisal in simulated gastric fluid after release as pure crystalline material compared to release from a disintegrating hydrogel composed of 25% by volume acetal cross-linker at both a low and high drug loading level.
Figure 8:
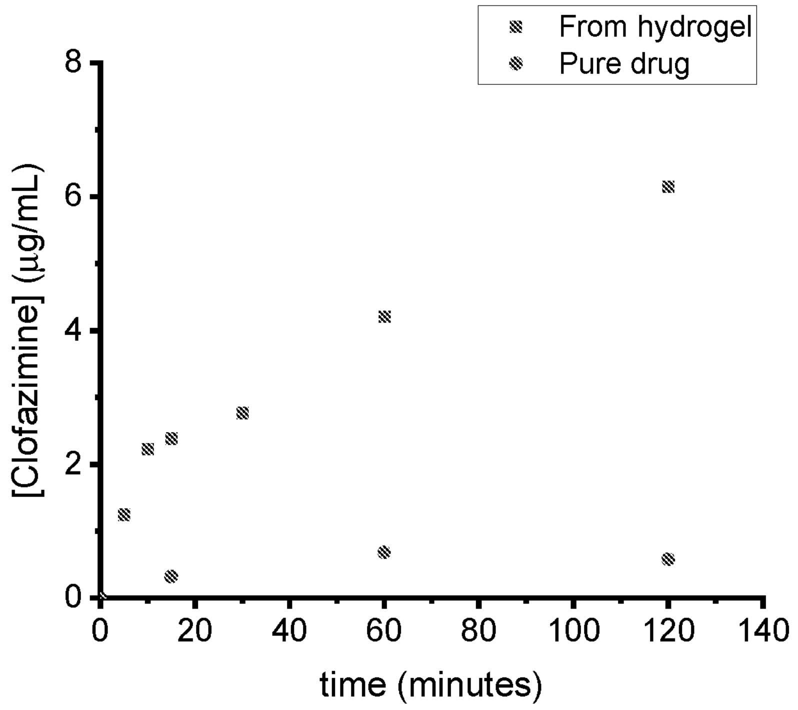
FIG. 8 is a dissolution profile of the concentration of clofazimine in simulated gastric fluid after release as pure crystalline material compared to release from a disintegrating hydrogel composed of 25% by volume acetal cross-linker.
Figure 9:
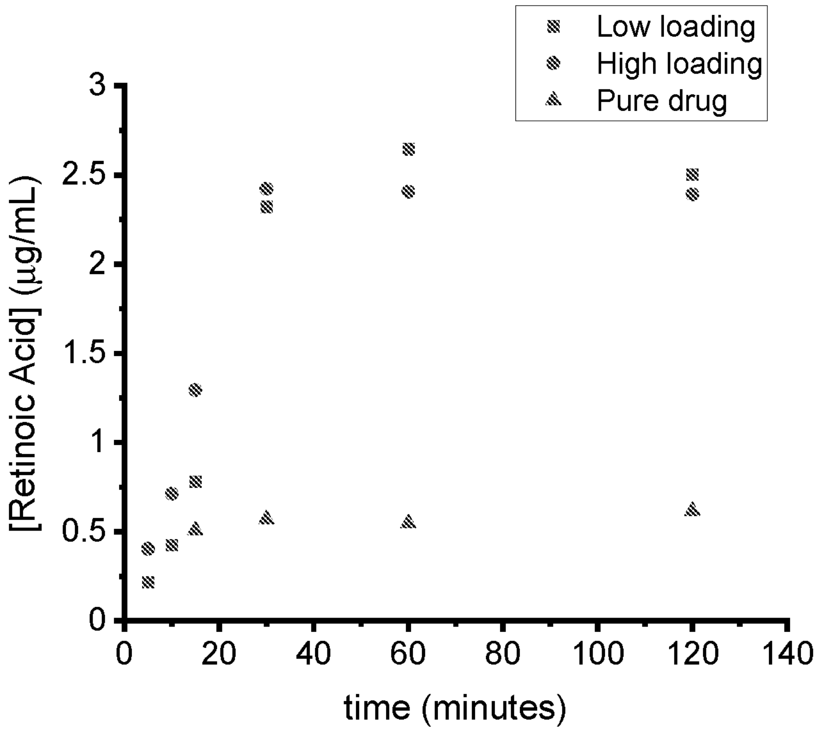
FIG. 9 is a dissolution profile of the concentration of retinoic acid in simulated gastric fluid after release as pure material compared to release from a disintegrating hydrogel composed of 25% by volume acetal cross-linker at both a low and high drug loading level.
Figure 10:
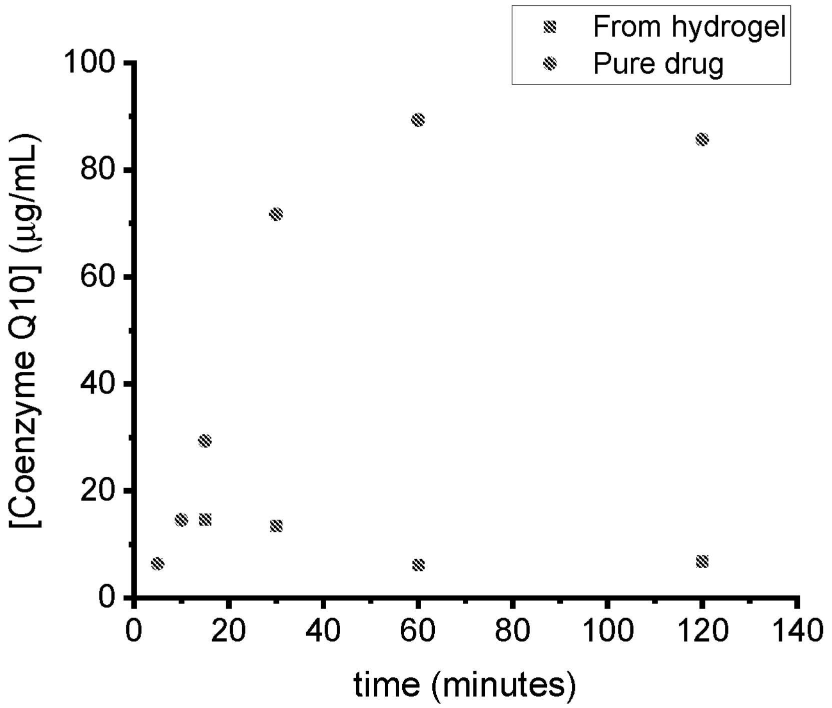
FIG. 10 is a dissolution profile of the concentration of coenzyme Q10 in simulated gastric fluid after release as pure crystalline material compared to release from a disintegrating hydrogel composed of 25% by volume acetal cross-linker, 0.7% by volume of methyl methacrylate, 2.2% by volume of dimethylaminoethyl methacrylate, and 1.1% by volume of butyl methacrylate.
Figure 11:
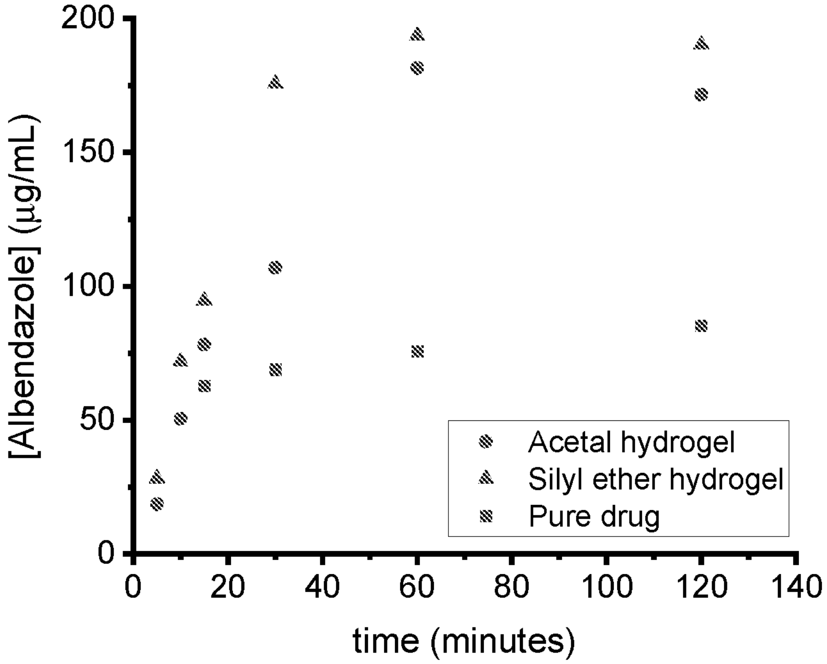
FIG. 11 is a dissolution profile of the concentration of albendazole in simulated gastric fluid after release as pure crystalline material compared to release from a disintegrating hydrogel composed of 25% by volume acetal cross-linker and composed of 30% by volume silyl ether cross-linker.
Figure 12:
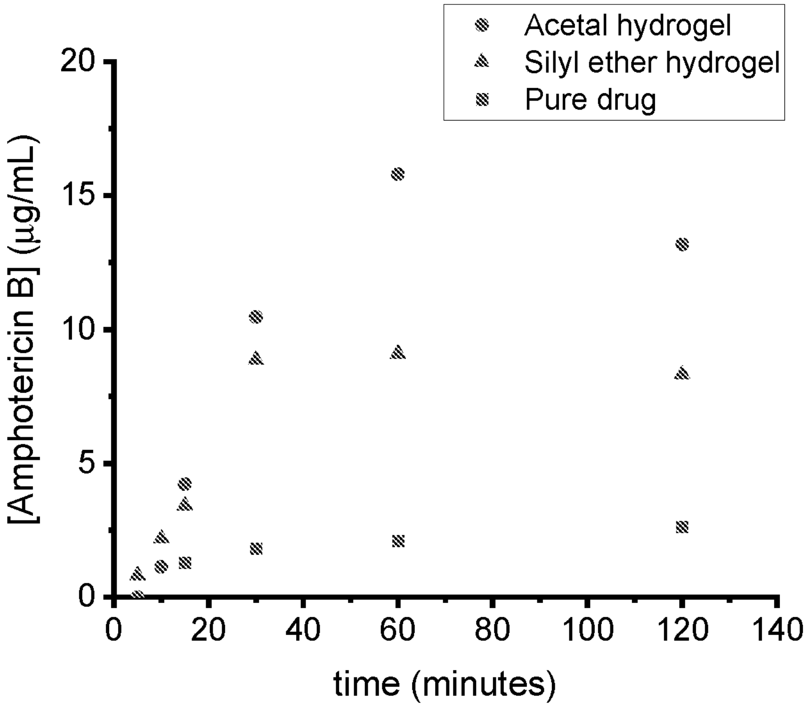
FIG. 12 is a dissolution profile of the concentration of amphotericin B in simulated gastric fluid after release as pure crystalline material compared to release from a disintegrating hydrogel composed of 25% by volume acetal cross-linker and composed of 30% by volume silyl ether cross-linker.
Figure 13:
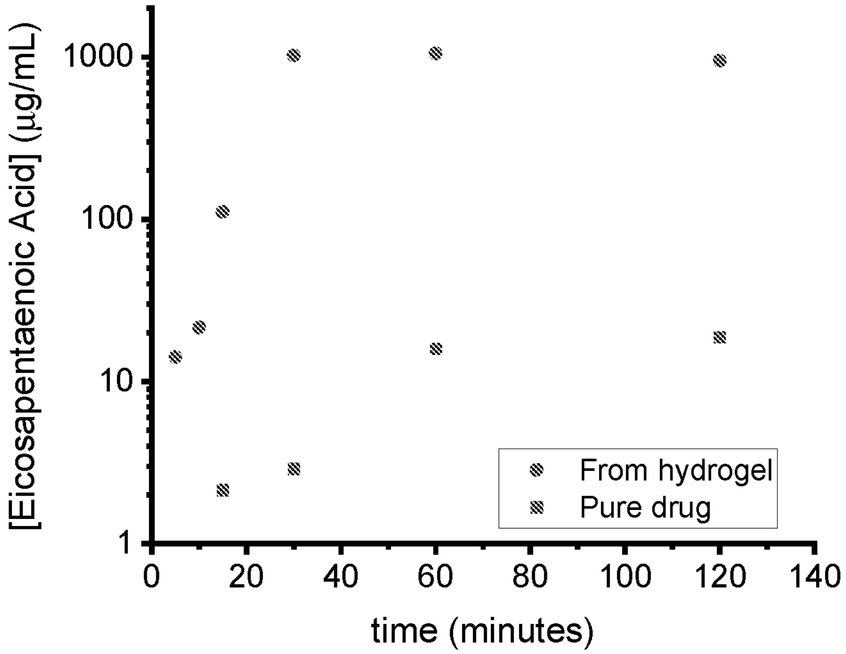
FIG. 13 is a dissolution profile of the concentration of eicosapentaenoic acid in simulated gastric fluid after release as pure material compared to release from a disintegrating hydrogel composed of 25% by volume acetal cross-linker.
Figure 14:
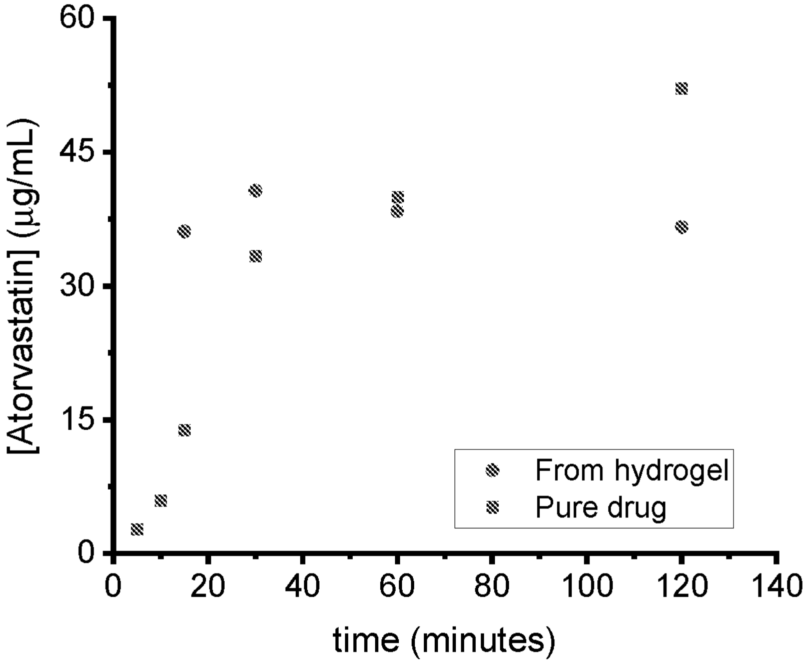
FIG. 14 is a dissolution profile of the concentration of atorvastatin in simulated gastric fluid after release as pure crystalline material compared to release from a disintegrating hydrogel composed of 25% by volume acetal cross-linker.
Figure 15:
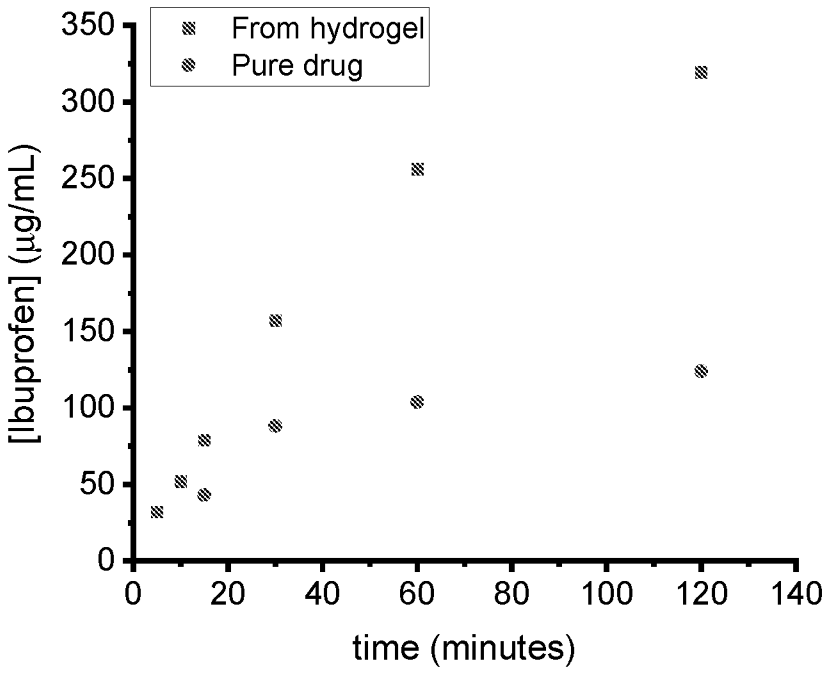
FIG. 15 is a dissolution profile of the concentration of ibuprofen in simulated gastric fluid after release as pure crystalline material compared to release from a disintegrating hydrogel composed of 25% by volume acetal cross-linker.
Figure 16:
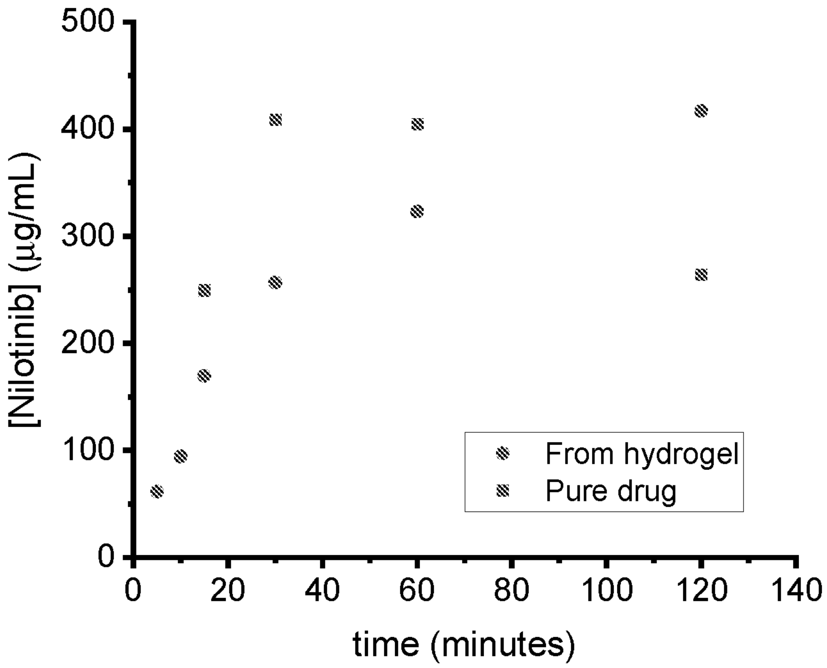
FIG. 16 is a dissolution profile of the concentration of nilotinib in simulated gastric fluid after release as pure crystalline material compared to release from a disintegrating hydrogel composed of 25% by volume acetal cross-linker.
Figure 17:
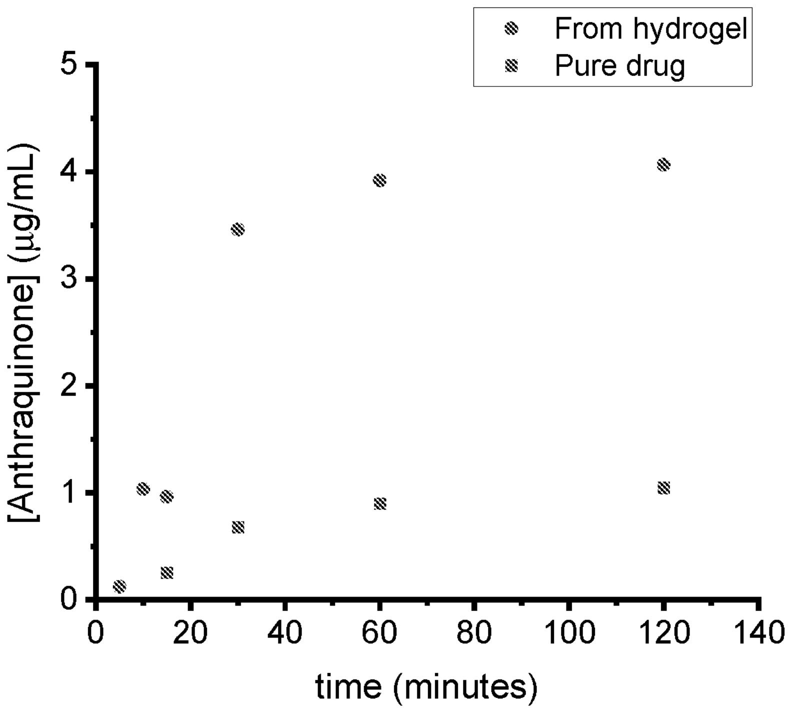
FIG. 17 is a dissolution profile of the concentration of anthraquinone in simulated gastric fluid after release as pure crystalline material compared to release from a disintegrating hydrogel composed of 25% by volume acetal cross-linker.
Figure 18:
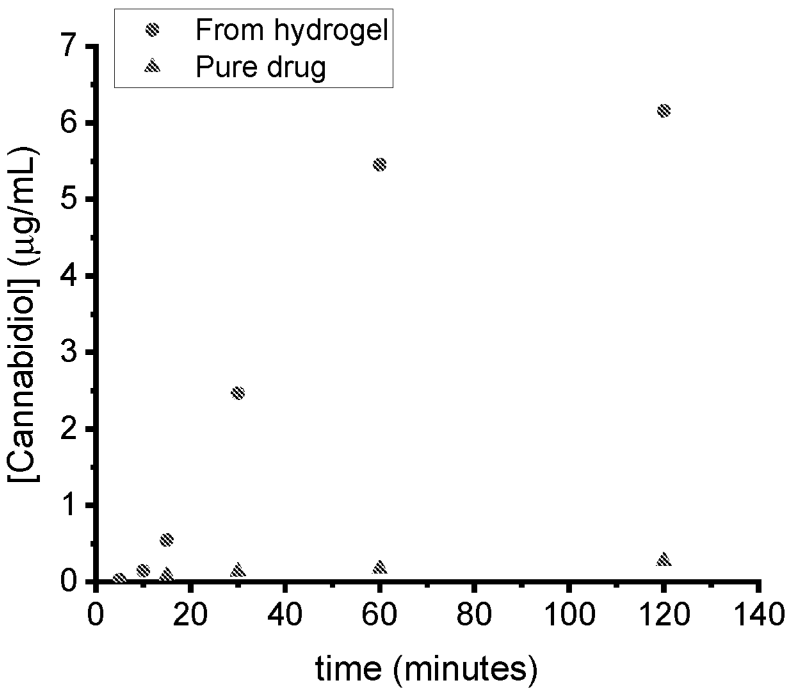
FIG. 18 is a dissolution profile of the concentration of cannabidiol in simulated gastric fluid after release as pure crystalline material compared to release from a disintegrating hydrogel composed of 25% by volume acetal cross-linker.
Figure 19:
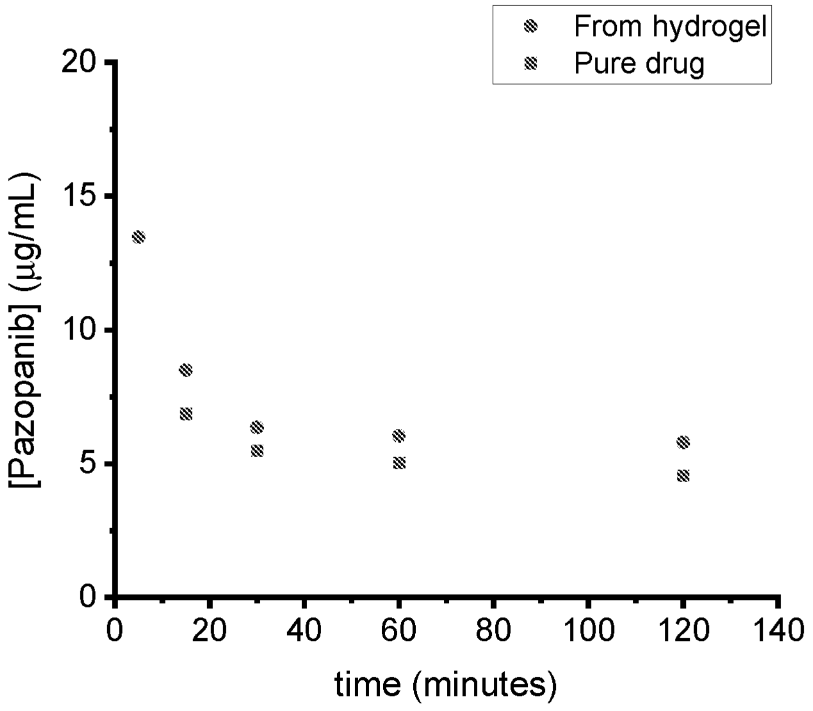
FIG. 19 is a concentration profile of pazopanib upon transition to fasted state simulated intestinal fluid after release into simulated gastric fluid as pure crystalline material compared to release from a disintegrating hydrogel composed of 25% by volume acetal cross-linker.

A hydrogel composed purely of triethylene glycol di[ethyl-1-methacryloyloxy poly(ethylene glycol) acetal] cross-linker was loaded with varying volumes of a solution of 200 mg/mL lumefantrine in dimethylformamide, resulting in a series of hydrogels containing lumefantrine ranging from 10% to 59% by weight. The tablets were dissolved in simulated gastric fluid and resulted in varying levels of supersaturation above the natural solubility of lumefantrine. The highest level of supersaturation achieved was 13 times the saturation concentration, as shown in FIG. 6, at a drug loading level of 29% by weight.

Example 4—Tocopherol (Vitamin E) in Disintegrating Hydrogels

Figure 3:
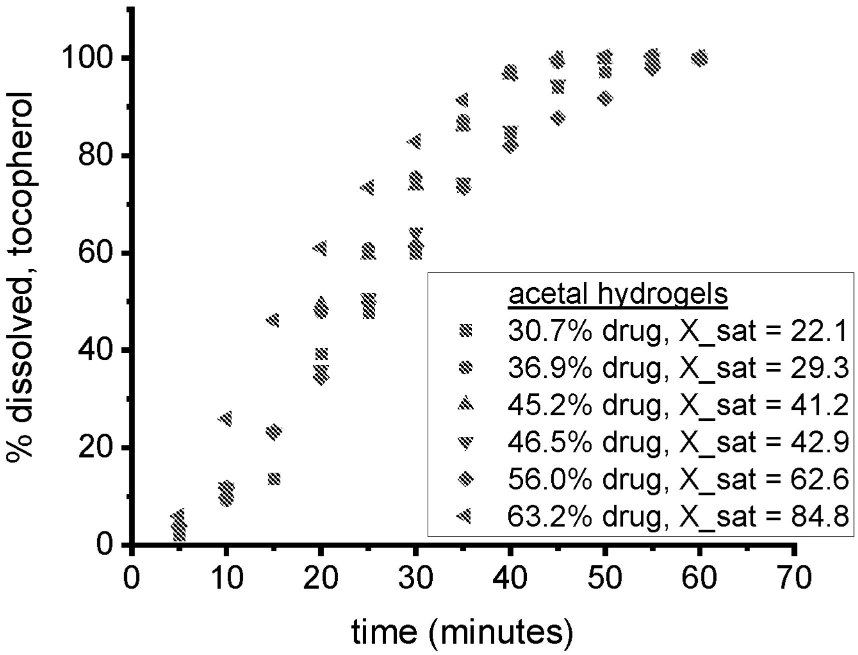
FIG. 3 is a dissolution profile of vitamin E (tocopherol) encapsulated at various drug loading levels in hydrogels composed of 25% by volume acetal cross-linker into a 0.1M HCl solution (pH=1). The ratio of the final concentration to the intrinsic solubility of vitamin E (X_sat) varies with the level of drug loading.
Figure 4:
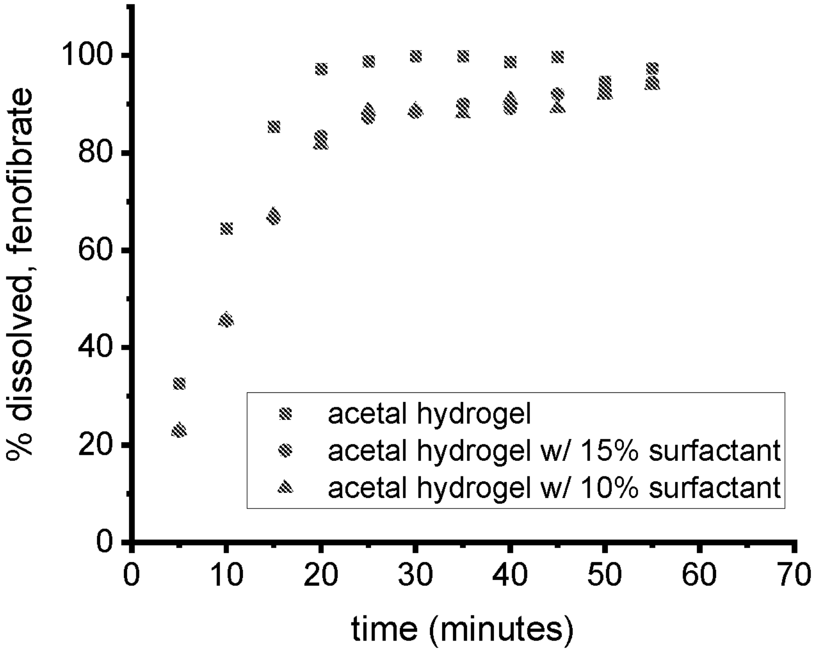
FIG. 4 is a dissolution profile of fenofibrate encapsulated in hydrogels composed of 20% by volume acetal cross-linker with either 0%, 15%, or 10% by volume surfactant into a 0.1M HCl solution (pH=1).
Figure 5:
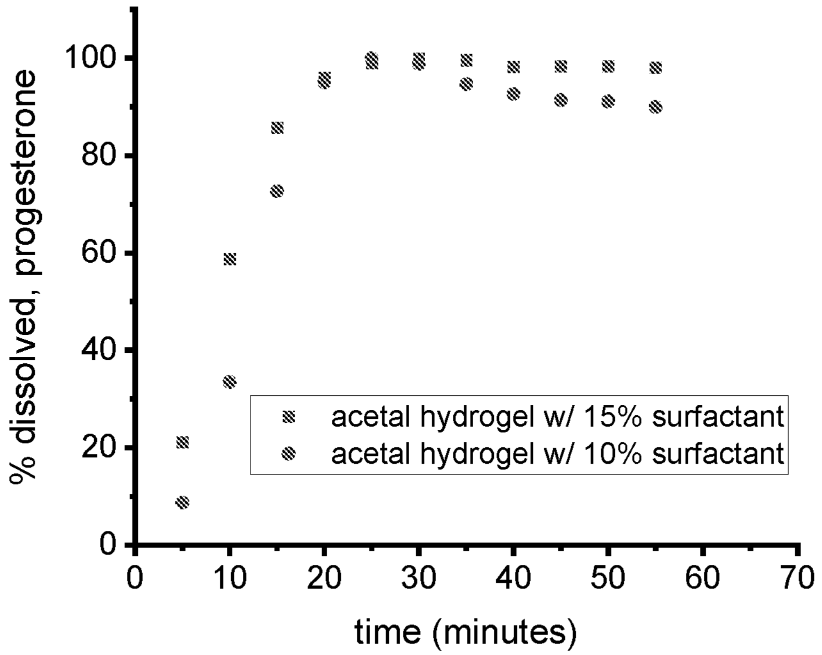
FIG. 5 is a dissolution profile of progesterone encapsulated in hydrogels composed of 20% by volume acetal cross-linker with either 15% by volume or 10% by volume surfactant into a 0.1M HCl solution (pH=1).

A hydrogel composed purely of triethylene glycol di[ethyl-1-methacryloyloxy poly(ethylene glycol) acetal] cross-linker was loaded with varying volumes of a solution of 400 mg/mL tocopherol in ethanol, resulting in a series of hydrogels containing tocopherol ranging from 30.7% to 63.2% by weight. The tablets were dissolved in simulated gastric fluid and resulted in varying levels of supersaturation above the natural solubility of tocopherol. The corresponding levels of supersaturation achieved after drug release varied from about 13 to about 74 times the saturation concentration, as shown in FIG. 3.

Example 5—Loading Disintegrating Hydrogels with an Active Pharmaceutical Ingredient and Releasing it in Physiologically Relevant Buffers A disintegrating hydrogel is first formed from 0.125 mL of a solution of dimethylformamide containing 25% by volume of the cross-linker triethylene glycol di[ethyl-1-methacryloyloxy poly(ethylene glycol) acetal] and 5% by volume of the photoinitiator 2-hydroxy-2-methylpropiophenone then purified by washing several times in ethanol. This disintegrating hydrogel is then transferred to the same solvent used to maximize the dissolution of the active pharmaceutical ingredient of interest. The hydrogel is transferred to a silicone mold and heated for a minimum amount of time to evaporate a majority of the solvent soaked into the hydrogel pores. Then about 0.1 mL of a solution of the active pharmaceutical ingredient solubilized in the preferred solvent is added to the silicone mold containing the hydrogel, which is allowed to swell in order to absorb the solution. Once absorbed, the solvent is removed in a vacuum oven in order to induce the crystallization of the active pharmaceutical ingredient in the hydrogel pores. The mass of the active pharmaceutical ingredient contained in the disintegrating hydrogel is determined experimentally then normalized by the combined mass of both components to quantify the weight fraction of the active pharmaceutical ingredient. These values for several active pharmaceutical ingredients are summarized in the column labelled "% wt drug" in Table 1.

Separately in a glass vial, seated on top of a stir plate with a stir bar that is set to rotate at 150 rotations per minute, is filled with a volume (in mL) of simulated gastric fluid equal to the quantity of active pharmaceutical ingredient (in mg) contained in the drug-loaded disintegrating hydrogel. The hydrogel is added to the vial and allowed to dissolve over the course of 2 hours. The presence of the active pharmaceutical ingredient in the aqueous solution is monitored by ultraviolet-visible spectrometry to quantify the concentration relative to the inherent solubility of the active pharmaceutical ingredient without a hydrogel present. The ratio of the solubility achieved upon release from disintegrating hydrogels to the solubility achieved upon dissolution without disintegrating hydrogels is the supersaturation. Values of supersaturation for several active pharmaceutical ingredients are summarized in the column labelled "X_sat" in Table 1.

As shown in the figures, vitamin E (tocopherol), fenofibrate, progesterone, and Lumefantrine, all poorly soluble APIs, encapsulated in immediate release versions of acid-catalyzed hydrolytically degradable hydrogels in a 0.1M HCl solution (pH=1) demonstrating the release of 80% of the encapsulated drug in no more than 40 minutes. The final concentration of each drug substance reached a supersaturation level of up to 74, 351, and 11 times the intrinsic solubility of each substance, respectively, due to the solubility enhancing properties of the hydrogel degradation products. The hydrogel labelled acetal hydrogel [w/ 10% surfactant] {w/ 15% surfactant} were synthesized by polymerizing a pre-cursor solution containing 25% [20%] {20%} by volume of the triethylene glycol di[ethyl-1-methacryloyloxy poly(ethylene glycol) acetal] cross-linker, 0% [3.9%] {3.9%} by volume of methyl methacrylate, 0% [6.1%] {6.1%} by volume of dimethylaminoethyl methacrylate, and 0% [10%] {15%} by volume of a hydrolytically hydrolysable surfactant monomer: acetaldehyde-(stearyl PEG-20 ether)-(acrylate ethylene glycol) acetal. Each drug substance is loaded into the pores of the hydrogel by first dissolving in ethanol and adding the organic solution into a silicone mold containing the pre-formed and washed hydrogel followed by evaporation of the solvent. Sufficient drug substance solution is added to the mold to reach a range of drug loading values.

Example 6—Synthesis of the Hydrolysable Surfactant Monomer Acetaldehyde-(Stearyl PEG-20 Ether)-(Acrylate Ethylene Glycol) Acetal Synthesis of the hydrolysable surfactant monomer acetaldehyde-(stearyl PEG-20 ether)-(acrylate ethylene glycol) acetal proceeds by first synthesizing the intermediate 2-acryloyloxy-ethanol vinyl ether. This intermediate is synthesized by combining acryloyl chloride with 1 molar equivalent of ethylene glycol vinyl ether in dichloromethane with 3 molar equivalents of triethylamine. This solution is allowed to react for 12 hours at 25° C. The resulting triethylammonium chloride salt is filtered from the solution and the residual trimethylamine and dichloromethane are removed via evaporation to yield the crude intermediate.

The hydrolysable surfactant monomer product is synthesized by combining 2-acryloyloxy-ethanol vinyl ether with 1 molar equivalent of the non-ionic surfactant stearyl PEG-20 ether in the solvent dichloromethane containing toluenesulfonic acid as a catalyst. This solution is allowed to react for 1 hour at 25° C. The reaction is quenched with the addition of 5 molar equivalents of triethylamine to the toluenesulfonic acid. The reaction solution is washed with an equal volume of 1M sodium hydroxide solution to extract the triethylammonium toluenesulfonate salt and excess triethylamine. The remaining reaction solution is dried to remove residual water then the product is purified by removing dichloromethane via evaporation.

What is claimed is:

1. A hydrogel comprising:

multi-component backbone polymer chains comprising poly(ethylene glycol) methacrylate and alkyl methacrylate monomers;

and a hydrolytically degradable linkage comprising hydrolytically degradable functional groups covalently bound to and connecting the poly(ethylene glycol) methacrylate monomers of two or more of said backbone polymer chains, wherein hydrolysis of the hydrolytically degradable functional groups releases the multi-component backbone polymer chains, wherein the hydrogel completely hydrolyzes and dissolves in no more than 60 minutes when added to an aqueous buffer at pH 1.

2. The hydrogel of claim 1, wherein the alkyl methacrylate monomers comprise methyl methacrylate, ethyl methacrylate, butyl methacrylate, cetyl methacrylate, or lauryl methacrylate.

3. The hydrogel of claim 1, wherein each hydrolytically degradable functional group comprises an acetal, anhydride, boronate ester, enamine, hydrazone, imide, imine, ketal, oxime, alkyl silyl ether, polysiloxanes, or silyl ether.

4. The hydrogel of claim 1, wherein each hydrolytically degradable functional group comprises at least one of a ketal or acetal functional group.

5. The hydrogel of claim 1, wherein the hydrogel envelops a payload comprising a nutritional supplement, active pharmaceutical ingredient, or cell-based supplement or therapy such that it can serve as an oral dosage form for these materials.

6. The hydrogel of claim 5, wherein the active pharmaceutical ingredient contained within the hydrogel void space is a kinase inhibitor, statin, hormone, antioxidant, macrolide, NSAID, anti-infective, retinoid, cannabinoid, anthracycline, or hyperlipidemic.

7. The hydrogel of claim 5, wherein the active pharmaceutical ingredient has a lipophilic partition coefficient ranging from 0.5 to 10.5, a melting temperature ranging from −54° C. to 301° C., and/or a molecular weight ranging from 174 g/mol to 1203 g/mol.

8. The hydrogel of claim 5, wherein the active pharmaceutical ingredient is present at a content of between 1% and 90% by weight.

9. The hydrogel of claim 1, wherein the backbone polymer chains contain 1% to 50% by mole of the alkyl methacrylate monomers.

10. The hydrogel of claim 1, wherein the hydrogel defines a void space containing a self-emulsifying or spontaneous micelle forming lipid solution.

11. The hydrogel of claim 10, wherein the lipid solution also contains an active pharmaceutical ingredient.

12. The hydrogel of claim 1, further comprising a payload encapsulated between the backbone polymer chains.

13. The hydrogel of claim 12, wherein the payload comprises one or more of a food grade material, supplement, pharmaceutical, nutraceutical, therapeutic, active ingredient, or combination thereof.

14. The hydrogel of claim 5, wherein the aqueous solubility (C_s) of the active pharmaceutical ingredient ranges from 0.01 μg/mL to 120 μg/mL.

15. The hydrogel of claim 1, wherein the hydrogel completely hydrolyzes and dissolves in no more than 30 minutes when added to an aqueous buffer at pH 1.

16. A hydrogel comprising:

multi-component backbone polymer chains comprising methacrylate and alkyl methacrylate monomers, and hydrolytically degradable linkages comprising hydrolytically degradable functional groups and poly(ethylene glycol) groups, wherein the hydrolytically degradable linkages are bound to and connecting methacrylate moieties of two or more of the multi-component backbone polymer chains, and wherein hydrolysis of the hydrolytically degradable functional groups releases the multi-component backbone polymer chains and poly(ethylene glycol) groups covalently bound thereto, and wherein the hydrogel completely hydrolyzes and dissolves in no more than 60 minutes when added to an aqueous buffer at pH 1.

17. The hydrogel of claim 1, wherein the multi-component backbone polymer chains released upon hydrolysis of the hydrolytically degradable linkages are amphiphilic.

18. The hydrogel of claim 5, wherein the hydrogel envelops an active pharmaceutical ingredient and, upon hydrolysis in aqueous solution, the solubility of the active pharmaceutical ingredient in the aqueous solution is improved as compared to the solubility of the active pharmaceutical ingredient in the aqueous solution in the absence of the hydrogel.

19. A hydrogel comprising:

(a) cross-linkers each comprising two or more methacrylate functional groups, and a linkage between the methacrylate functional groups, wherein the linkage comprises a hydrolytically degradable functional group; and (b) alkyl methacrylate monomers;

wherein the methacrylate functional groups of the cross-linkers and the alkyl methacrylate monomers are polymerized to provide multi-component backbone polymer chains;

wherein the cross-linkers comprise a central poly(ethylene glycol) segment of molecular weight no less than 150 g/mol with both terminal hydroxyl groups attached to an acetal functional group with a PEG methacrylate with a molecular weight no less than 174 g/mol;

and wherein the multi-component backbone polymer chains are released upon degradation of the hydrolytically degradable functional group.

20. The hydrogel of claim 19, wherein the alkyl methacrylate monomers comprise methyl methacrylate, ethyl methacrylate, butyl methacrylate, octyl methacrylate, dodecyl methacrylate, or octadecyl methacrylate.

21. The hydrogel of claim 19, wherein the hydrolytically degradable cross-linkers comprise triethylene glycol di[ethyl-1-methacryloyloxy poly(ethylene glycol) acetal].

22. The hydrogel of claim 19, wherein the hydrogel comprises between 1% and 50% by mole of the hydrolytically degradable cross-linker.

23. The hydrogel of claim 19, wherein the hydrogel comprises between 10% and 30% by mole of the hydrolytically degradable cross-linker.

24. The hydrogel of claim 19, wherein hydrogel comprises between 1% and 50% by mole of the hydrolytically degradable cross-linker and the remainder alkyl methacrylate monomers.

25. The hydrogel of claim 19, wherein the hydrogel comprises between 1% and 50% by mole triethylene glycol di [ethyl-1-methacryloyloxy poly(ethylene glycol) acetal] cross-linker, and the remainder alkyl methacrylate monomers.

26. The hydrogel of claim 24, wherein the alkyl methacrylate monomers comprise methyl methacrylate, ethyl methacrylate, butyl methacrylate, octyl methacrylate, dodecyl methacrylate, or octadecyl methacrylate.

27. The hydrogel of claim 25, wherein the alkyl methacrylate monomers comprise methyl methacrylate, ethyl methacrylate, butyl methacrylate, octyl methacrylate, dodecyl methacrylate, or octadecyl methacrylate.

28. The hydrogel of claim 24, wherein the alkyl methacrylate monomers comprise methyl methacrylate or butyl methacrylate.

29. The hydrogel of claim 25, wherein the alkyl methacrylate monomers comprise methyl methacrylate or butyl methacrylate.

30. The hydrogel of claim 19, wherein the hydrolytically degradable functional groups comprise an acetal, anhydride, boronate ester, enamine, hydrazone, imide, imine, ketal, oxime, alkyl silyl ether, polysiloxanes, or silyl ether.

* * * * *